United States Patent
Peyman et al.

(10) Patent No.: US 6,992,187 B2
(45) Date of Patent: Jan. 31, 2006

(54) PROCESS FOR THE PREPARATION OF BIRTHONECTIN RECEPTOR ANTAGONISTS

(75) Inventors: Anuschirwan Peyman, Kelkheim (DE); Gerrit Schubert, Kelkheim (DE)

(73) Assignee: Aventis Pharma Deutschland GmbH, (DE)

( * ) Notice: Subject to any disclaimer, the term of this patent is extended or adjusted under 35 U.S.C. 154(b) by 70 days.

(21) Appl. No.: 10/363,450

(22) PCT Filed: Aug. 29, 2001

(86) PCT No.: PCT/EP01/09985

§ 371 (c)(1),
(2), (4) Date: Apr. 1, 2003

(87) PCT Pub. No.: WO02/18384

PCT Pub. Date: Mar. 7, 2002

(65) Prior Publication Data

US 2004/0248907 A1    Dec. 9, 2004

(30) Foreign Application Priority Data

Aug. 31, 2000  (DE) ................. 100 42 655

(51) Int. Cl.
 *C07D 473/40*  (2006.01)
 *C07D 519/00*  (2006.01)
 *C07D 239/49*  (2006.01)
 *C07D 401/12*  (2006.01)

(52) U.S. Cl. ............... 544/264; 544/277; 544/329; 544/332

(58) Field of Classification Search ............... 544/277, 544/264, 329, 332
See application file for complete search history.

(56) References Cited

U.S. PATENT DOCUMENTS 6,743,800 B1 *   6/2004   Peyman et al. ......... 514/263.22

FOREIGN PATENT DOCUMENTS

| EP | 0434450 | 6/1991 |
|---|---|---|
| EP | 0853084 | 7/1998 |
| EP | 1065207 | 1/2001 |
| EP | 1065208 | 1/2001 |
| JP | 11080131 A * | 3/1999 |

* cited by examiner

*Primary Examiner*—Mark L. Berch
(74) *Attorney, Agent, or Firm*—Charles A. Muserlian

(57) ABSTRACT

A process for the preparation of a compound of the formula

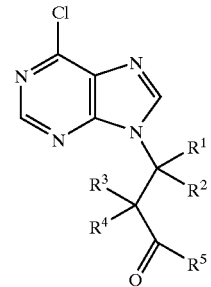

(IV)

wherein the substituents are defined as in the specification.

15 Claims, No Drawings

PROCESS FOR THE PREPARATION OF BIRTHONECTIN RECEPTOR ANTAGONISTS

This application is a 371 of PCT/EP01/09985 filed Aug. 29, 2001.

The present invention relates to a process for the preparation of vitronectin receptor antagonists of the formula (I) by linkage of a 9-chloropurine of the formula (IV) to a 4-substituted piperidine and comprises an efficient method for the preparation of compounds of the formula (IV).

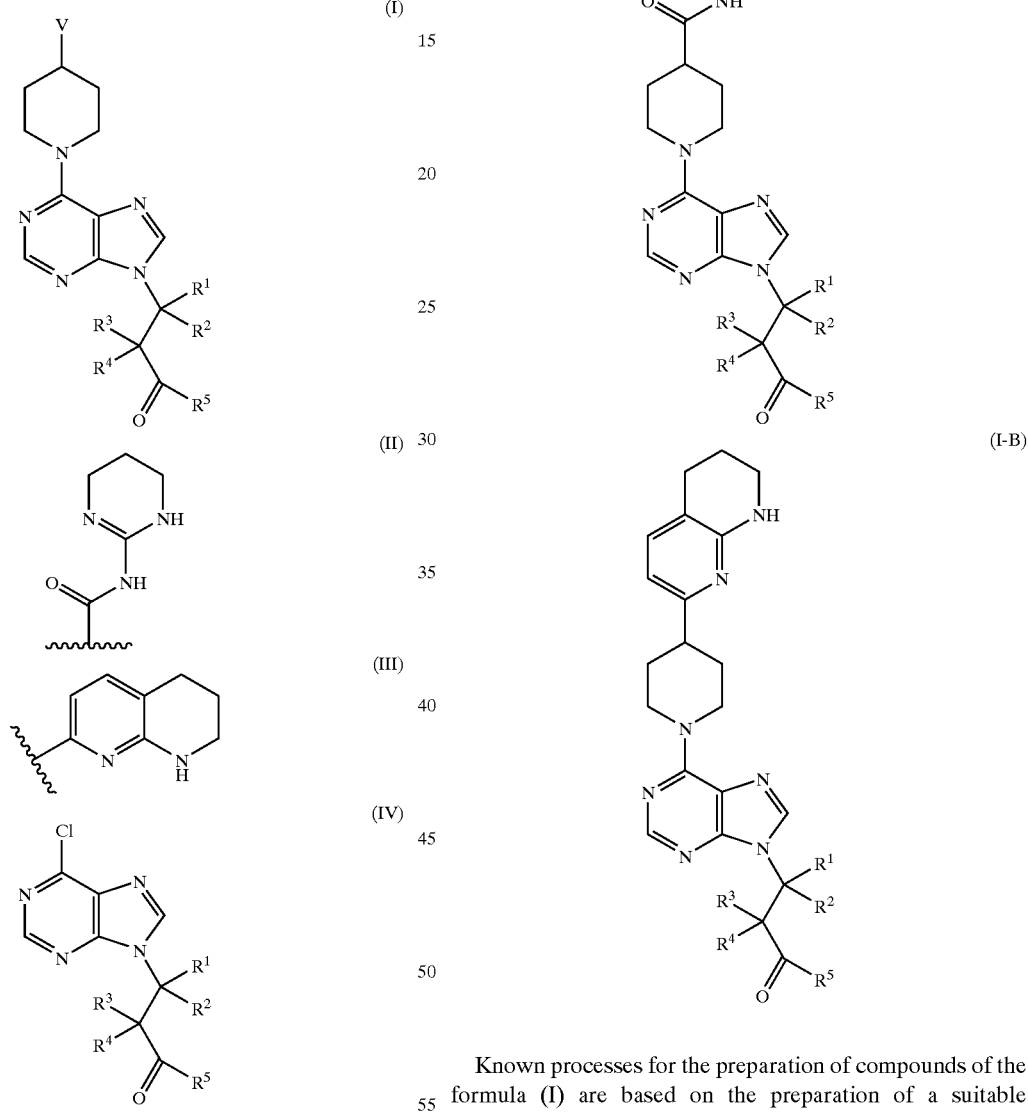

Inhibitors of cell adhesion and in particular antagonists of the vitronectin receptor are of especial interest in the pharmaceutical industry as they can be used for the treatment of a series of diseases (Hillis et al., Clinical Science 91 (1996) 639; Engleman et al., Ann. Rep. Med. Chem. 31 (1996) 191; Samanen et al., Current Pharm. Design 3 (1997) 545).

In European patent applications EP 0853084, EP 1065207 (EP 99112636.8) and EP 1065208 (EP 99112637.6), vitronectin receptor antagonists of the formula (I) are described in which V is the radicals of the formulae (II) or (III).

Compounds of the formula (I) in which V is a radical of the formula (II) are designated below as compounds of the formula (I-A). Compounds of the formula (I) in which V is a radical of the formula (III) are designated below as compounds of the formula (I-B).

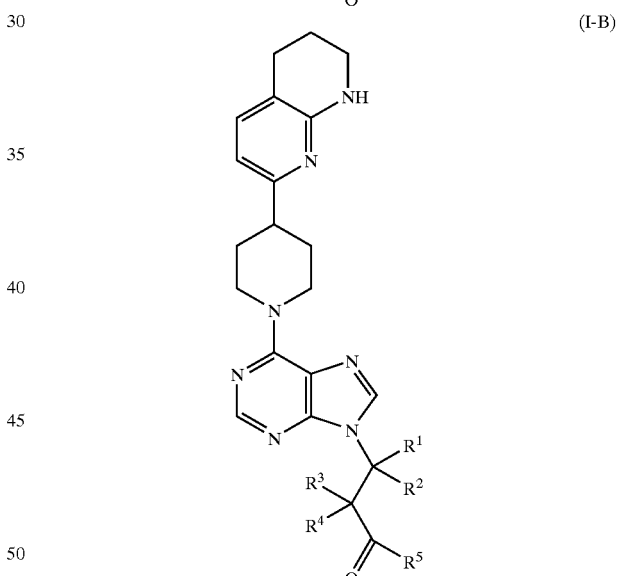

Known processes for the preparation of compounds of the formula (I) are based on the preparation of a suitable 9-substituted purine derivative having a nucleophilically substitutable leaving group in the 6-position, for example of a 6-chloropurine derivative of the formula (IV), which is converted into a compound of the formula (I) in several steps by reaction with a 4-substituted piperidine derivative.

The compounds of the formula (IV) needed are prepared in only low yields by alkylation in the 9-position of the purine structure via a Mitsunobu reaction and require laborious chromatographic purifications (EP 1065207 (EP 99112636.8)). The process is therefore not suitable for syntheses on a relatively large scale.

It is an object of the present invention to find a more efficient process for the synthesis of compounds of the formula (I).

The object is achieved by a novel process for the preparation of compounds of the formula (I) comprising an efficient method for the synthesis of compounds of the formula (IV) and a process based on this for the preparation of compounds of the formula (I).

One subject of the invention is thus a process for the preparation of a compound of the formula (IV), which comprises first reacting the 5-nitropyrimidine of the formula (V) by a method known to the person skilled in the art (see source literature in March, Advanced Organic Chemistry, Fourth Edition, John Wiley & Sons, 1992; or Kelley, J. Med. Chem. 33 (1990) 196) with a primary amine of the formula (VI) to give a compound of the formula (VII),

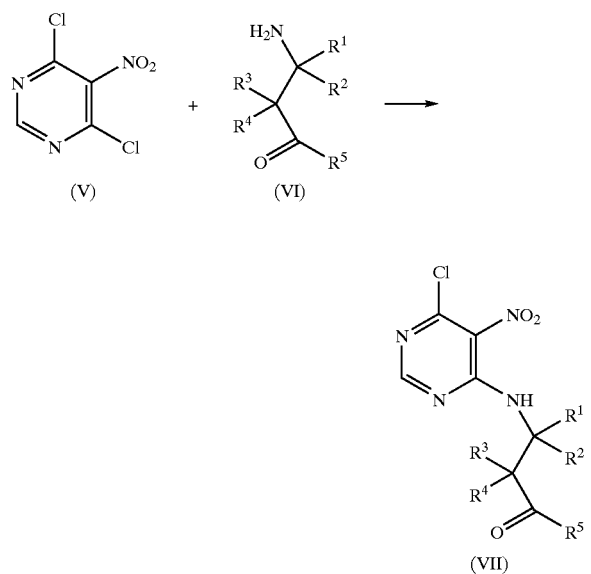

the reaction preferably being carried out in a suitable organic solvent, for example ethanol, isopropanol, butanol, DCM, CHCl$_3$, THF, diethyl ether, n-heptane, n-hexane, n-pentane, cyclohexane, diisopropyl ether, methyl tert-butyl ether, acetonitrile, DMF, DMSO, dioxane, toluene, benzene, EA, or a mixture of two or more of these solvents, preferably in THF, if appropriate with addition of a base such as butyllithium, LDA, sodium hydride, sodium amide, potassium tert-butoxide, CaCO$_3$, Cs$_2$CO$_3$, TEA, DIPEA, complex bases (sodium amide-R$^{12}$ONa, where R$^{12}$ is (C$_2$–C$_6$)-alkyl or CH$_3$CH$_2$OCH$_2$CH$_2$), it also being possible for an excess of (VI) to serve as base. The reaction is in general carried out at temperatures from −20 to 150° C., preferably at temperatures from −20 to 100° C.

In a subsequent step, the compound of the formula (VII) is reduced by a process known to the person skilled in the art (March, Advanced Organic Chemistry, Fourth Edition, John Wiley & Sons, 1992; R. C. Larock, Comprehensive Organic Transformations, VCH, Weinheim, 1989) to give a compound of the formula (VIII),

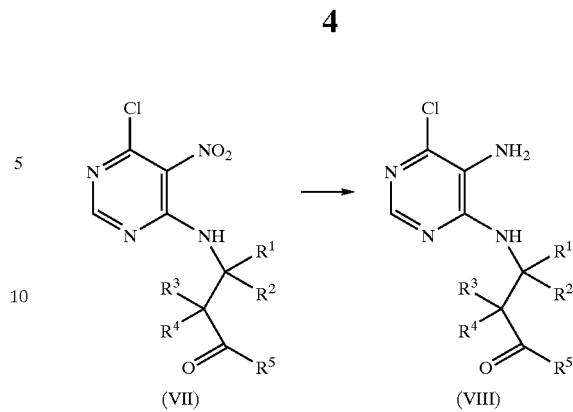

for example by catalytic hydrogenation by means of Raney nickel or palladium or by reduction using SnCl$_2$. The catalytic hydrogenation is optionally carried out in a suitable organic solvent, such as ethanol; methanol, acetic acid, THF, diethyl ether, n-heptane, n-hexane, n-pentane, cyclohexane, diisopropyl ether, methyl tert-butyl ether, dioxane, EA or in a mixture of two or more of these solvents, preferably in ethanol or methanol, for example at temperatures from 0 to 100° C. and at hydrogen pressures from 1 to 10 bar. The reaction with SnCl$_2$ is preferably carried out in a suitable organic solvent such as ethanol, methanol, DCM, CHCl$_3$, THF, diethyl ether, n-heptane, n-hexane, n-pentane, cyclohexane, diisopropyl ether, methyl tert-butyl ether, acetonitrile, DMF, DMSO, N-methylpyrrolidone, dioxane, toluene, benzene, EA or in a mixture of two or more of these solvents, preferably in ethanol, for example at temperatures from 0 to 100° C. preferably from 50 to 100° C.

In a further step, the compound of the formula (VIII) is cyclized by a method known to the person skilled in the art (March, Advanced Organic Chemistry, Fourth Edition, John Wiley & Sons, 1992; or Kelley, J. Med. Chem. 33 (1990) 196) by means of a C$_1$ unit to give a compound of the formula (IV),

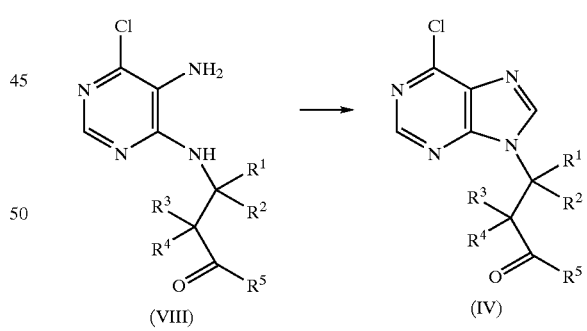

where the C$_1$ unit is, for example, a formic acid derivative, preferably a tri-(C$_1$–C$_4$)-alkyl orthoformate, particularly preferably triethyl orthoformate, and where the reaction is optionally carried out in the presence of an acid, such as an alkylsulfonic or arylsulfonic acid, trifluoroacetic acid, trichloroacetic acid, dichloroacetic acid, an acidic ion exchanger, HCl, preferably ethanesulfonic acid, and where furthermore the reaction is optionally carried out in a suitable organic solvent such as THF, diethyl ether, n-heptane, n-hexane, n-pentane, cyclohexane, diisopropyl ether, methyl tert-butyl ether, acetonitrile, DMF, DMSO, NMP, dioxane, toluene, benzene, EA or a mixture of two or more of these solvents.

In the compounds of the formulae (I), (I-A), (I-B), (IV), (VI), (VII) and (VIII), $R^1$, $R^2$, $R^3$, $R^4$ independently of one another are hydrogen, fluorine, chlorine, CN, $(C_1-C_{14})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $R^6$—O—$R^7$, $R^6R^{6'}N$—$R^7$, $R^6C(O)R^7$, $R^6S(O)_2N(R^9)R^7$, $R^6OC(O)N(R^9)R^7$, $R^6C(O)N(R^5)R^7$, $R^6N(R^9)C(O)N(R^9)R^7$, $R^6N(R^9)S(O)_2N(R^9)R^7$, $R^6S(O)_2R^7$, $R^6SC(O)N(R^9)R^7$, $R^6N(R^9)C(O)R^7$, $R^6N(R^9)S(O)_2R^7$, $R^6N(R^9)R^7$ or a 3-membered to 7-membered, saturated or unsaturated ring which can contain one or two heteroatoms such as nitrogen, sulfur and oxygen and which can be unsubstituted or mono- or disubstituted by =O, =S and $R^8$, where alkyl, cycloalkyl and aryl radicals can be mono- or polysubstituted by fluorine, chlorine, bromine, $CF_3$, CN, $R^6N(R^9)R^7$; $R^6R^{6'}NR^7$, $R^6C(O)R^7$, $R^6N(R^9)C(O)R^7$, $R^6N(R^9)S(O)_2R^7$, $R^6$, $R^6$—O—$R^7$;

$R^5$ is hydroxyl, $(C_1-C_8)$-alkoxy, $(C_5-C_{14})$-aryl-$(C_1-C_8)$-alkoxy-, $(C_1-C_8)$-alkylcarbonyloxy-$(C_1-C_4)$-alkoxy-, $(C_3-C_{14})$-cycloalkoxy or $(C_3-C_{14})$-cycloalkyl-$(C_1-C_8)$-alkoxy-;

$R^6$, $R^{6'}$ independently of one another are $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl- or a 3-membered to 7-membered, saturated or unsaturated ring which can contain one or two heteroatoms, such as nitrogen, sulfur and oxygen, and is unsubstituted or mono- or disubstituted by =O, =S and $R^8$, where aryl, cycloalkyl and alkyl radicals can be substituted once, twice or three times by fluorine, chlorine, bromine, cyano, $CF_3$, nitro, carboxyl, $(C_1-C_6)$-alkyl, $(C_1-C_6)$-alkoxy, $(C_5-C_{14})$-aryl, $(C_1-C_6)$-alkoxy-$(C_1-C_6)$-alkyl-, $(C_1-C_6)$-alkoxycarbonyl, $(C_1-C_6)$-alkylcarbonyl, $(C_1-C_6)$-alkylaminocarbonyl, $(C_1-C_6)$-alkoxy-$(C_1-C_6)$-alkoxy-, $(C_5-C_{14})$-aryl-$(C_1-C_6)$-alkylcarbonyl, $(C_1-C_6)$-alkanoylamino, $(C_5-C_{14})$-arylsulfonylamino, $(C_1-C_6)$-alkylsulfonylamino, $(C_1-C_6)$-alkylamino, di-$((C_1-C_6)$-alkyl)amino, $(C_1-C_6)$-alkylsulfonyl, $(C_1-C_6)$-alkylaminosulfonyl, $(C_6-C_{14})$-aryl-$(C_1-C_6)$-alkylaminosulfonyl or $(C_5-C_{14})$-aryl-$(C_1-C_6)$-alkylsulfonyl;

$R^7$ independently of one another is $(C_1-C_4)$-alkanediyl or a direct bond;

$R^8$ is $(C_1-C_{14})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, fluorine, chlorine, bromine, cyano, $CF_3$, nitro, carboxyl, $(C_1-C_6)$-alkoxy, $(C_1-C_6)$-alkoxy-$(C_1-C_6)$-alkyl-, $(C_1-C_6)$-alkoxycarbonyl, $(C_1-C_6)$-alkylcarbonyl, $(C_1-C_6)$-alkylaminocarbonyl, $(C_1-C_6)$-alkoxy-$(C_1-C_6)$-alkoxy-, $(C_5-C_{14})$-aryl-$(C_1-C_6)$-alkylcarbonyl, $(C_1-C_6)$-alkanoylamino, $(C_5-C_{14})$-arylsulfonylamino, $(C_1-C_6)$-alkylsulfonylamino, $(C_1-C_6)$-alkylamino, di-$(C_1-C_6)$-alkylamino, $(C_1-C_6)$-alkylsulfonyl, $(C_1-C_6)$-alkylaminosulfonyl, $(C_6-C_{14})$-aryl-$(C_1-C_6)$-alkylaminosulfonyl or $(C_5-C_{14})$-Aryl-$(C_1-C_6)$-alkylsulfonyl; and $R^9$ is hydrogen or $(C_1-C_4)$-alkyl.

The alkyl radicals occurring in the substituents can be straight-chain or branched, saturated or mono- or polyunsaturated. This also applies if they carry substituents or occur as substituents of other radicals, for example in alkoxy, alkoxycarbonyl or arylalkyl. The same applies to alkanediyl radicals.

Unsaturated alkyl radicals and alkanediyl radicals are, for example, alkenyl, alkenylene, alkynyl and alkynylene radicals. Examples of alkenyl radicals are vinyl, 1-propenyl, allyl, butenyl, 3-methyl-2-butenyl, examples of alkynyl radicals are ethynyl, 1-propynyl or propargyl. Examples of alkenylene radicals are vinylene or propenylene, examples of alkynylene radicals are ethynylene or propynylene. Alkenylene and alkynylene radicals can be straight-chain or branched.

Examples of alkyl radicals are: methyl, ethyl, propyl, butyl, pentyl, hexyl, heptyl, octyl, decyl, undecyl, dodecyl, tridecyl, hexadecyl, octadecyl, isopropyl, isobutyl, isopentyl, neopentyl, isohexyl, 3-methylpentyl, 2,3,4-trimethylhexyl, sec-butyl, tert-butyl, tert-pentyl. Preferred alkyl radicals are methyl, ethyl, propyl, isopropyl, butyl, sec-butyl and tert-butyl.

Cycloalkyl radicals can be monocyclic, bicyclic or tricyclic. Monocyclic cycloalkyl radicals are, in particular, cyclopropyl, cyclobutyl, cyclopentyl, cyclohexyl, cycloheptyl and cyclooctyl, which, however, can also be substituted by, for example, $(C_1-C_4)$-alkyl. 4-Methylcyclohexyl and 2,3-dimethylcyclopentyl may be mentioned as examples of substituted cycloalkyl radicals.

Bicyclic and tricyclic cycloalkyl radicals can be unsubstituted or can be substituted in any desired suitable positions, for example by one or more oxo groups and/or one or more identical or different $(C_1-C_4)$-alkyl groups, such as methyl or isopropyl groups, preferably methyl groups. The free bond of the bicyclic or tricyclic radical can be situated in any desired position of the molecule; the radical can thus be bonded via a bridgehead atom or an atom in a bridge. The free bond can also be situated in any desired stereochemical position, for example in an exo or an endo position.

Examples of parent structures of bicyclic ring systems are norbornane (=bicyclo[2.2.1]heptane), bicyclo[2.2.2]octane and bicyclo[3.2.1]octane. An example of a parent bicyclic system substituted by an oxo group is camphor (=1,7,7-trimethyl-2-oxobicyclo[2.2.1]heptane). Examples of parent structures of tricyclic systems are twistane (=tricyclo[4.4.0.0$^{3,8}$]decane, adamantane (=tricyclo[3.3.1.1$^{3,7}$]decane), noradamantane (=tricyclo[3.3.1.0$^{3,7}$]nonane), tricyclo[2.2.1.0$^{2,6}$]heptane, tricyclo[5.3.2.0$^{4,9}$]dodecane, tricyclo[5.4.0.0$^{2,9}$]undecane or tricyclo[5.5.1.0$^{3,11}$]tridecane. An adamantyl radical can be 1-adamantyl or 2-adamantyl.

Aryl is, for example, carbocyclic $(C_6-C_{14})$-aryl radicals such as phenyl, naphthyl, biphenylyl, anthryl or fluorenyl, preferably phenyl, 1-naphthyl, 2-naphthyl, particularly preferably phenyl. If not stated otherwise, aryl radicals, in particular phenyl radicals, can be mono- or polysubstituted, preferably mono-, di- or trisubstituted, independently of one another by radicals from the group consisting of $(C_1-C_8)$-alkyl, in particular $(C_1-C_4)$-alkyl, $(C_1-C_8)$-alkoxy, in particular $(C_1-C_4)$-alkoxy, halogen, such as fluorine, chlorine and bromine, nitro, amino, trifluoromethyl, hydroxyl, methylenedioxy, cyano, hydroxycarbonyl, aminocarbonyl, $(C_1-C_4)$-alkoxycarbonyl, phenyl, phenoxy, benzyl, benzyloxy, tetrazolyl, $(R^{10}O)_2P(O)$ or $(R^{10}O)_2P(O)$—O—, where $R^{10}$=H, $(C_1-C_{10})$-alkyl, $(C_5-C_{14})$-aryl or $(C_5-C_{14})$-aryl-$(C_1-C_8)$-alkyl-. The same applies to the corresponding arylene radicals.

In monosubstituted phenyl radicals, the substituent can be situated in the 2-position, 3-position or 4-position, the 3-position and 4-position being preferred. If phenyl is disubstituted; the substituents can be in the 2,3-, 2,4-, 2,5-, 2,6-, 3,4- or 3,5-position. Preferably, in disubstituted phenyl radicals the two substituents are arranged in the 3,4-position relative to the site of linkage.

Aryl and arylene groups can furthermore be monocyclic or polycyclic heteroaromatic ring systems, in which 1, 2, 3, 4 or 5 carbon atoms can be rep(aced by heteroatoms from the group consisting of N, O and S, such as 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl, or a benzofused, cyclopenta-fused, cyclohexa-fused or cyclohepta-fused derivative of these radicals such as benzoxazolyl, benzothiazolyl or benzimidazolyl. These heterocycles can be substituted by the same substituents as the abovementoned carbocyclic aryl systems.

Among these heteroaryl groups and the corresponding heteroarylene groups, monocyclic or bicyclic aromatic ring systems having 1, 2 or 3 heteroatoms from the group consisting of N, O, S, which can be substituted by 1, 2 or 3 substituents from the group consisting of $(C_1-C_6)$-alkyl, $(C_1-C_6)$-alkoxy, F, Cl, $NO_2$, $NH_2$, $CF_3$, hydroxyl, $(C_1-C_4)$-alkoxycarbonyl, phenyl, phenoxy, benzyloxy and benzyl, are preferred. Particularly preferred are monocyclic or bicyclic aromatic ring systems having 1, 2 or 3 heteroatoms from the group consisting of N, O, S, which can be substituted by 1 or 2 substituents from the group consisting of $(C_1-C_4)$-alkyl, $(C_1-C_4)$-alkoxy, phenyl, phenoxy, benzyl and benzyloxy.

Examples of 3-membered, 4-membered, 5-membered, 6-membered and 7-membered, saturated or unsaturated rings which can contain one or two heteroatoms, such as nitrogen, sulfur and oxygen, and are optionally mono- or disubstituted by =O, =S and $R^8$, are cyclopropane, cyclobutane, cyclopentane, cyclohexane, cycloheptane, cyclopentene, cyclohexene, cycloheptene, tetrahydropyran, 1,4-dioxacyclohexane, morpholine, piperazine, piperidine, pyrrolidine, dihydroisoxazole, tetrahydroisoxazole, 1,3-dioxolane, 1,2-dithiolane, 2,3-dihydrofuran, 2,5-dihydrofuran, tetrahydrofuran, 2,3-dihydrothiophene, 2,5-dihydrothiophene, 2-imidazoline, 3-imidazoline, 4-imidazoline, 2-oxazoline, 3-oxazoline, 4-oxazoline, 2-thiazoline, 3-thiazoline, 4-thiazoline, thiazolidine, α-thiapyran, α-pyran, γ-pyran.

The invention preferably relates to a process for the preparation of compounds of the formula (IV) wherein
$R^1$, $R^2$, $R^3$, $R^4$ independently of one another are hydrogen, $(C_1-C_{14})$-alkyl, $(C_3-C_{14})$-cycloalkyl, $(C_3-C_{14})$-cycloalkyl-$(C_1-C_8)$-alkyl-$(C_5-C_{14})$-aryl, $(C_5-C_{14})$-aryl-$(C_1-C_8)$-alkyl-, $R^6R^{6'}N-R^7$, $R^6S(O)_2N(R^9)R^7$, $R^6N(R^9)S(O)_2N(R^9)R^7$, $R^6OC(O)N(R^9)R^7$, $R^6C(O)N(R^9)R^7$, $R^6N(R^9)R^7$ or a 3-membered to 7-membered, saturated or unsaturated ring which can contain one or two heteroatoms, such as nitrogen, sulfur and oxygen and which can optionally be mono- or disubstituted by =O, =S and $R^8$, where alkyl, cycloalkyl and aryl radicals can be mono- or polysubstituted by fluorine, chlorine, bromine, $CF_3$, CN and $R^6-O-R^7$;

$R^5$ is hydroxyl or $(C_1-C_4)$-alkoxy;

$R^6$, $R^{6'}$ independently of one another are $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl- or a 3-membered to 7-membered, saturated or unsaturated ring which can contain one or two heteroatoms, such as nitrogen, sulfur and oxygen and which can optionally be mono- or disubstituted by =O, =S and $R^8$;

where aryl, cycloalkyl and alkyl radicals can be mono- to trisubstituted by fluorine, chlorine, bromine, cyano, $CF_3$, $(C_1-C_6)$-alkyl, $(C_1-C_6)$-alkoxy, $(C_5-C_{14})$-aryl, $(C_1-C_6)$-alkoxy-$(C_1-C_6)$-alkyl-, $(C_1-C_6)$-alkoxycarbonyl, $(C_1-C_6)$-alkylcarbonyl;

$R^7$ independently of one another is $(C_1-C_4)$-alkylene or a direct bond;

$R^8$ is $(C_1-C_{14})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, fluorine, chlorine, bromine, $CF_3$, $(C_1-C_6)$-alkoxy or $(C_1-C_6)$-alkoxy-$(C_1-C_6)$-alkyl-; and $R^9$ is hydrogen or $(C_1-C_4)$-alkyl.

The invention particularly preferably relates to a process for the preparation of compounds of the formula (IV) wherein $R^1$, $R^2$, $R^3$, $R^4$ independently of one another are hydrogen, $R^6S(O)_2N(R^9)R^7$ or $R^6OC(O)N(R^9)R^7$;

$R^5$ is $(C_1-C_4)$-alkoxy, preferably ethoxy or tert-butoxy;

$R^6$ is $(C_5-C_{14})$-aryl, preferably 1-naphthyl, or $(C_5-C_{14})$-aryl-$(C_1-C_8)$-alkyl-, preferably benzyl;

$R^7$ is a direct bond; and $R^9$ is hydrogen.

By reaction with compounds of the formula (IX-A) or (IX-B), the compounds of the formula (IV) then yield the compounds of the formula (I-A) or (I-B).

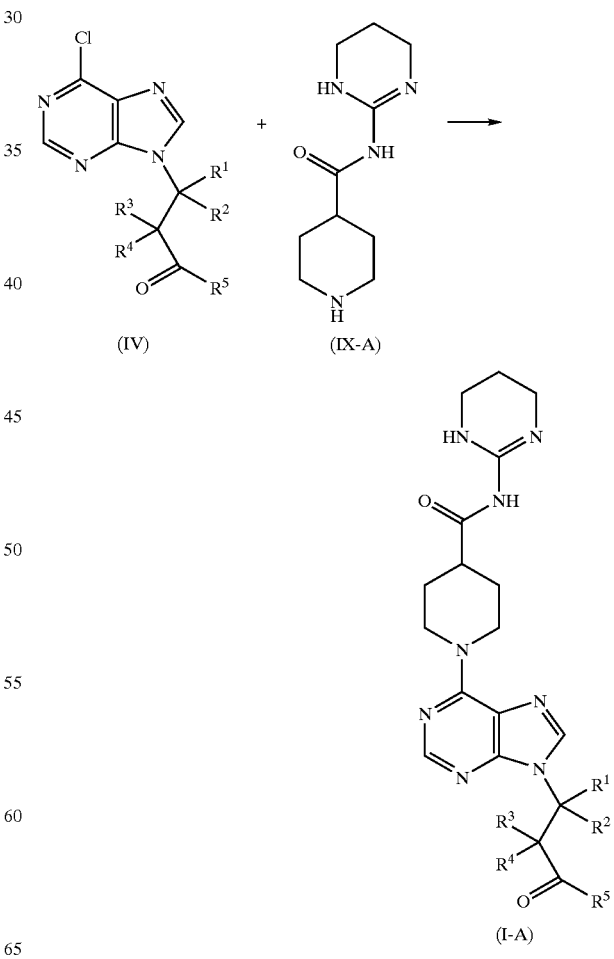

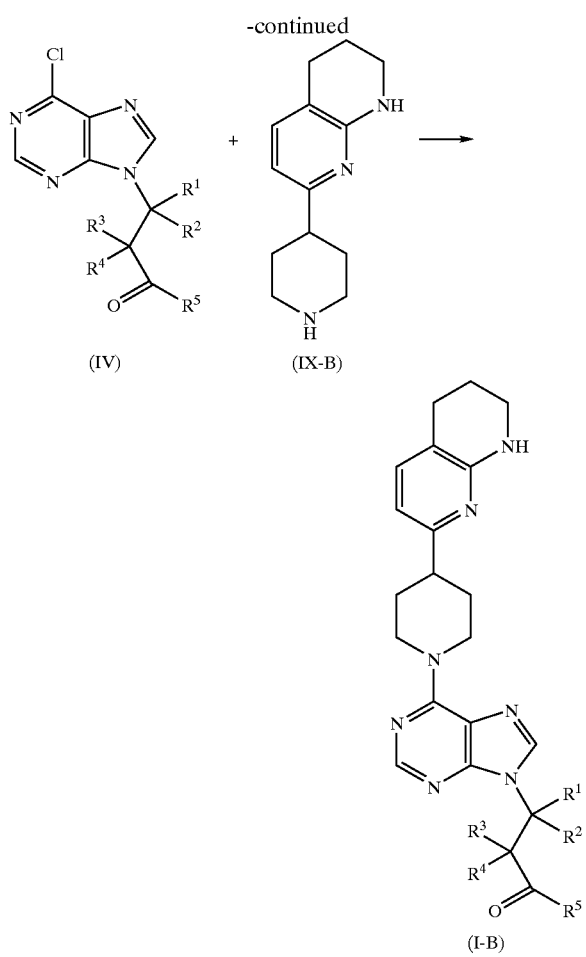

(IV)  (IX-B)

(I-B)

A subject of the invention also is a process for the preparation of the compounds of the formula (I-A), which comprises reacting a compound of the formula (IV) with a compound of the formula (IX-A).

A subject of the invention furthermore is the use of the compounds of the formula (IV) for the production of pharmaceutical active compounds, which comprises reacting a compound of the formula (IV) with a compound of the formula (IX-A) to give a compound of the formula (I-A), or reacting a compound of the formula (IV) with a compound of the formula (IX-B) to give a compound of the formula (I-B), compounds of the formula (I-B) being excluded in which $R^1$ and $R^2$ are hydrogen, one of the radicals $R^3$ and $R^4$ is benzyl-O—C(O)—NH— and the other is hydrogen, and $R^5$ is hydroxyl or tert-butoxy.

The compounds of the formula (I-A) and (I-B) are preferably prepared in a single step, if appropriate in a suitable organic solvent, by methods known to the person skilled in the art (see source literature in March, Advanced Organic Chemistry, Fourth Edition, John Wiley & Sons, 1992). Suitable organic solvents are, for example, DCM, CHCl$_3$, THF, diethyl ether, n-heptane, n-hexane, n-pentane, cyclohexane, diisopropyl ether, methyl tert-butyl ether, acetonitrile, DMF, DMSO, N-methylpyrrolidone, dioxane, toluene, benzene, EA or mixtures of two or more of these solvents, preferably DMF. The reaction is preferably carried out with addition of a base such as butyllithium, lithium diisopropylamide (LDA), sodium hydride, sodium amide, potassium tert-butoxide, CaCO$_3$, Cs$_2$CO$_3$, triethylamine, diisopropylethylamine, complex bases (sodium amide-$R^{12}$ONa, where $R^{12}$ is (C$_2$–C$_6$)-alkyl or CH$_3$CH$_2$OCH$_2$CH$_2$), where, however, an excess of (IX) can also serve as a base. The reaction is particularly preferably carried out in the presence of triethylamine (TEA) or diisopropylethylamine (DIPEA), for example at temperatures from 0 to 150° C., preferably at temperatures from 25 to 120° C., particularly preferably at temperatures from 50 to 100° C. The above-defined preferred embodiments of the radicals $R^1$ to $R^9$ in the process for the preparation of compounds of the formula (IV) here correspondingly apply.

In contrast to the prior art, the process according to the invention gives good yields in a lower number of process steps and can advantageously be used for syntheses on a relatively large scale.

A further subject of the present invention relates to a process for the preparation of a compound of the formula (I-A) in which the compound of the formula (V) is reacted with a compound of the formula (VI), the compound of the formula (VII) obtained is reduced to the compound of a formula (VIII), the compound of the formula (VIII) obtained is reacted with a C$_1$ unit, and the compound of the formula (IV) obtained is reacted with a compound of the formula (IX-A) to give a compound of the formula (I-A), where all above definitions and explanations with respect to the radicals $R^1$ to $R^9$ and the reaction conditions correspondingly apply.

Another subject of the present invention relates to a process for the preparation of a compound of the formula (I-B), in which the compound of the formula (V) is reacted with a compound of the formula (VI), the compound of the formula (VII) obtained is reduced to a compound of the formula (VIII), the compound of the formula (VIII) obtained is reacted with a C$_1$ unit, and the compound of the formula (IV) obtained is reacted with a compound of the formula (IX-B) to give a compound of the formula (I-B), where all above definitions and explanations with respect to the radicals $R^1$ to $R^9$ and the reaction conditions correspondingly apply.

The invention further relates to a process for the preparation of a compound of the formula (IX-A), which comprises first reacting a compound of the formula (X) with 2-aminopyrimidine (XI) to give a compound of the formula (XII)

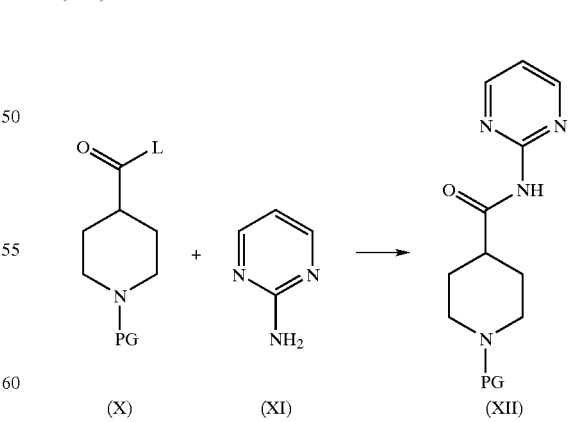

(X)  (XI)  (XII)

where PG is a suitable amino protective group (Greene, Wuts, Protective Groups in Organic Synthesis, John Wiley & Sons, 1999), for example tert-butoxycarbonyl or benzyloxycarbonyl, preferably tert-butoxycarbonyl, and L is a nucleophilically substitutable leaving group, for example chlorine, a pentafluorophenoxy, phenoxy, phenylthio, methylthio or 2-pyridylthio group, or a nitrogen heterocycle, for example 1-imidazolyl. L is particularly preferably a pentafluorophenoxy group. The compounds of the formula (XII) are preferably prepared in a manner known to the person skilled in the art (March, Advanced Organic Chemistry, Third Edition, John Wiley & Sons, 1985) either from the respective carboxylic acid chlorides (L=Cl) which can in turn be prepared in a manner known per se from the underlying carboxylic acids (L=OH) using, for example, thionyl chloride, or from other activated carboxylic acid derivatives such as from the methyl esters (L=OCH$_3$) which are obtainable from the acids by treating with gaseous HCl in methanol, from the imidazolides (L=1-imidazolyl) which are obtainable by treating the acids with carbonyldiimidazole (Staab, Angew. Chem. Int. Ed. Engl. 1 (1962) 351–367), or from mixed anhydrides (L=C$_2$H$_5$O—C(O)—O or TosO) which are obtainable with Cl—COOC$_2$H$_5$ or tosyl chloride in the presence of triethylamine in an inert solvent. The carboxylic acids can also be activated using dicyclohexylcarbodiimide (DCCI) or O-[(cyano(ethoxycarbonyl)-methylene)amino]-1,1,3,3-tetramethyluronium tetrafluoroborate (TOTU) or other activation reagents customary in peptide chemistry. A number of suitable methods for the preparation of activated carboxylic acid derivatives are indicated with details of source literature in J. March, Advanced Organic Chemistry, Third Edition, John Wiley & Sons, 1985, p. 350.

The preparation of the compounds of the formula (XII) by reaction of 2-aminopyrimidine (XI) with a compound of the formula (X) is particularly preferably be carried out in the presence of a base such as triethylamine, L especially preferably being a pentafluorophenoxy group.

The reaction of an activated carboxylic acid derivative of the formula (X) with 2-aminopyrimidine (XI) is particularly preferably carried out in a manner known per se in an inert, protic or aprotic polar organic solvent such as THF, dimethoxyethane, dioxane, DMF, NMP, but just so water can be used as a solvent with use of a base such as NaOH. Preferably an acid scavenger is added to remove acid formed, for example in the form of excess aminopyrimidine (XI).

In the process for the preparation of a compound (IX-A), the compound of the formula (XII) is then reduced according to a known process (see source literature in March, Advanced Organic Chemistry) to give a compound of the formula (XIII), for example by catalytic hydrogenation over palladium on carbon, the reaction optionally being carried out in a suitable organic solvent, such as ethanol, methanol, acetic acid, THF, diethyl ether, n-heptane, n-hexane, n-pentane, cyclohexane, diisopropyl ether, methyl tert-butyl ether, dioxane, EA or in a mixture of two or more of these solvents, preferably in ethanol or methanol, for example at temperatures from 0 to 100° C. and at hydrogen pressures from 1 to 10 bar.

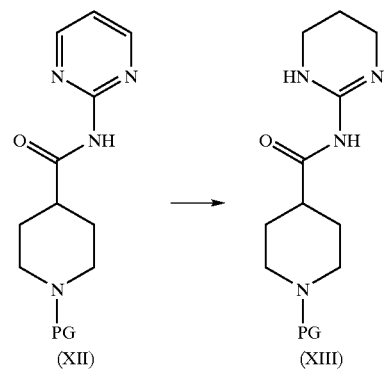

The compound of the formula (XIII) is then deprotected to give the compound of the formula (IX-A) (Greene, Wuts, Protective Groups in Organic Synthesis, John Wiley & Sons, 1999).

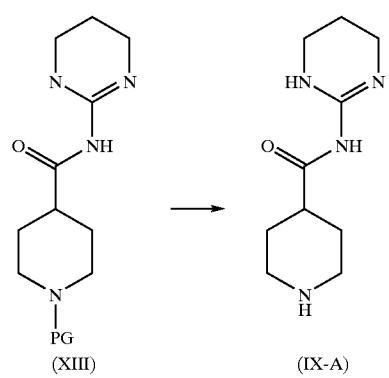

Advantageously, when using the benzyloxycarbonyl protective group the hydrogenation of the compound of the formula (XII) and the removal of the protective group to give the compound of the formula (IX-A) can be carried out simultaneously.

Alternatively, a compound (XIII) is obtained by reacting a compound of the formula (X) with 2-amino-1,4,5,6-tetrahydropyrimidine (XIV), where PG and L are as defined above. Bases and solvents which may optionally be added are those mentioned for the reaction of the compounds (X) and (XI). PG is preferably tert-butoxycarbonyl or benzyloxycarbonyl, L is preferably a pentafluorophenoxy group. The base added can be, for example, excess 2-amino-1,4,5,6-tetrahydropyrimidine (XIV) or triethylamine or diisopropylethylamine.

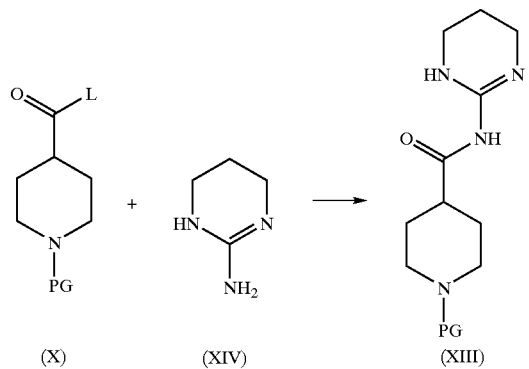

Depending on the manner of carrying out the process for the preparation and the work-up method, the compounds of the formulae (I-A), (I-B), (IV), (VI), (VII), (VIII), (IX-A), (IX-B), (XI), (XII), (XIII) and (XIV) can also be obtained as salts and/or employed as salts, for example as acid addition salts with inorganic acids or organic acids, such as hydrogen chloride, hydrogen bromide, sulfuric acid, acetic acid, p-toluenesulfonic acid etc.

In the processes described, compounds of the formulae (I-A), (I-B), (IV), (VI), (VII) and (VIII) can be obtained and/or employed as individual stereoisomers or as mixtures of two or more stereoisomers in all ratios, for example as R isomers or S isomers or racemates.

The invention also relates to the compounds of the formulae (VII), (VIII), (IX-A), (XII) and (XIII), in which the radicals $R^1$ to $R^5$ have the meanings indicated above, in all their stereoisomeric forms and mixtures thereof in all ratios, and their salts. In the preparation of compounds of the formulae (VII), (VIII), (IV), (XII), (XIII), (IX-A), (IX-B), (I-A) and (I-B), it can moreover generally be necessary in the course of the synthesis temporarily to block functional groups which in the respective synthesis step could lead to undesired reactions or side reactions, by means of a protective group strategy suited to the synthesis problem, which is known to the person skilled in the art (Greene, Wuts, Protective Groups in Organic Synthesis, John Wiley & Sons, 1999). Groups in the compounds can also be converted into one another, e.g. a group $R^5$=alkoxy can be converted into a group $R^5$=hydroxyl by means of an ester cleavage.

List of Abbreviations:

| abs. | absolute |
|---|---|
| Boc | tert-butyloxycarbonyl |
| DCCI | dicyclohexylcarbodiimide |
| DCM | dichloromethane |
| DIPEA | diisopropylethylamine |
| DMF | dimethylformamide |
| DMSO | dimethyl sulfoxide |
| EA | ethyl acetate |
| ES | electrospray ionization |
| L | nucleophilically substitutable leaving group |
| LDA | lithium diisopropylamide |
| NMP | N-methylpyrrolidone |
| PG | protective group for amines |
| sec | secondary |
| TEA | triethylamine |
| tert | tertiary |
| THF | tetrahydrofuran |
| Tos | tosyl |
| TOTU | O-[(cyano(ethoxycarbonyl)methylene)amino]-1,1,3,3-tetramethyluronium tetrafluoroborate |

EXAMPLES

1) Piperidine-4-carboxylic acid (1,4,5,6-tetrahydropyrimidin-2-yl)amide

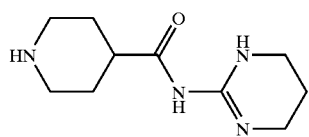

1a) 1-tert-Butyl 4-pentafluorophenyl piperidine-1,4-dicarboxylate 100 g (436 mmol) of piperidine-1,4-dicarboxylic acid 1-tert butyl ester were dissolved in 1.3 l of anhydrous THF, 39 ml of anhydrous pyridine were added and 86 ml (500 mmol) of pentafluorophenyl trifluoroacetate were added dropwise with stirring and with ice-cooling in the course of 30 minutes, and the mixture was allowed to stand at room temperature for 3 h. The solvent was then stripped off in vacuo and the residue was taken up in about 2 l of EA, extracted twice each with 0.5 N HCl, saturated $NaHCO_3$ solution and saturated NaCl solution, and the organic phase was dried over $Na_2SO_4$. After evaporating off the solvent in vacuo, an oil remained which crystallized after addition of heptane. Yield 151.5 g (88%), colorless crystals. M.p. 87–88° C. (heptane).

1b) tert-Butyl 4-(1,4,5,6-tetrahydropyrimidin-2-ylcarbamoyl) piperidine-1-carboxylate 29.2 g (73.9 mmol) of the compound of Example 1a) were dissolved in 200 ml of anhydrous dioxane, 15 ml of anhydrous triethylamine were added and a solution of 7.4 g (74.6 mmol) of 1,4,5,6-tetrahydropyrimidin-2-ylamine in 100 ml of anhydrous dioxane (dissolved with heating and cooled to room temperature again) were added at room temperature with stirring in the course of 10 minutes with slight cooling with ice, and the mixture was then allowed to stand overnight at room temperature. The solvent was evaporated in vacuo, the residue was taken up in about 200 ml of DCM, extracted twice each with about 200 ml of saturated citric acid solution, saturated $NaHCO_3$ solution and saturated NaCl solution, the organic phase was dried over $Na_2SO_4$ and the solvent was evaporated in vacuo. An oil remained which crystallized after addition of a EA/heptane mixture (about 1:1). Yield 20.92 g (91%), colorless crystals. M.p. 155–160° C. (heptane/EA).

1c) Piperidine-4-carboxylic acid (1,4,5,6-tetrahydropyrimidin-2-yl)amide bistrifluoroacetate 42.0 g (135.3 mmol) of the compound of Example 1b) were introduced into 200 ml of 95% trifluoroacetic acid with stirring and the mixture was stirred at 25 to 30° C. for 1 h. It was then evaporated in vacuo and the residue was evaporated twice in vacuo with about 100 ml of xylene each time. The semicrystalline residue was stirred with THF and then with diisopropyl ether and in each case filtered off with suction. Yield 32.0 g (54%), colorless crystals. M.p. 205–207° C. (decomposition with evolution of gas).

MS(ES$^+$): m/e=211 (100%, M+H$^+$).

$^1$H-NMR (400 MHz, DMSO): 1.73 (m, 2H), 1.85 (m, 2H), 1.95 (dd, 2H), 2.7 (m, 1H), 2.95 (bs, 2H), 3.3 (d, 2H), 3.4 (bs, 2H), 3.35–3.55 (2m, 6H, superimposed with H$_2$O signal), 8.55 (bs, 1H), 8.8 (bs, 1H), 9.35 (s, 2H), 12.1 (s, 1H) ppm.

2) Ethyl (2S)-3-(6-chloropurin-9-yl)-2-(naphthalene-1-sulfonylamino)propionate

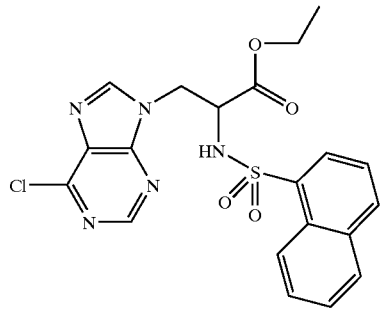

2a) Ethyl (2S)-3-(6-chloro-5-nitropyrimidin-4-ylamino)-2-(naphthalene-1-sulfonylamino)propionate 2.96 g (29.3 mmol) of triethylamine were added dropwise at −10° C. in the course of 5 minutes to 5.0 g (13.9 mmol) of ethyl (2S)-2-(naphthalene-1-sulfonylamino)-3-aminopropionate (EP 1070707 (EP 99114372.8)) and 2.84 g (14.6 mmol) of 4,6-dichloro-5-nitropyrimidine, dissolved in 140 ml of abs. THF. The mixture was stirred at −5° C. for 15 minutes and then at room temperature for 12 h. The reaction mixture was taken up in EA and extracted with a saturated aqueous NaCl solution, the organic phase was dried over MgSO$_4$ and filtered, and the solvent was distilled off in vacuo. For purification, the residue was chromatographed over silica gel (EA/heptane 3:7). Yield: 6.38 g.

MS(ES$^+$): m/e=482.2 (50%), 480.2 (100%).

$^1$H-NMR (200 MHz, CDCl$_3$): 1.12 (t, 3H), 3.80 (t, 2H), 4.03 (q, 2H), 4.23 (dt, 1H), 5.71 (d, 1H), 7.39–8.61 (m, 9H) ppm.

2b) Ethyl (2S)-3-(6-chloro-5-amino-pyrimidin-4-ylamino)-2-(naphthalene-1-sulfonylamino)propionate 12.6 g (66.5 mmol) of SnCl$_2$ were added to 6.38 g (13.3 mmol) of the compound of Example 2a) in 75 ml of ethanol and the reaction mixture was stirred at 70° C. for 30 minutes. It was then poured onto 30 g of ice, and the mixture was treated with 17 g of Na$_2$CO$_3$ and with 100 ml of EA and stirred for 15 min. The phases were separated, and the aqueous phase was extracted a further two times with EA. The combined organic phases were dried over MgSO4, filtered and the solvent was distilled off in vacuo. Yield: 5.2 g.

MS(ES$^+$): m/e=452.2 (40%), 450.2 (100%).

2c) Ethyl (2S)-3-(6-chloropurin-9-yl)-2-(naphthalene-1-sulfonylamino)propionate 5.2 g of the compound of Example 2b) were dissolved in 20 ml of N-methylpyrrolidone and 33.8 g of triethyl orthoformate and treated with 1.3 g of ethanesulfonic acid. The reaction mixture was diluted with EA and extracted twice with saturated K$_2$SO$_4$ solution, then with a saturated aqueous NaCl solution. The organic phase was dried over MgSO$_4$ and filtered and the solvent was distilled off in vacuo. For purification, the residue was chromatographed over silica gel (DCM/CH$_3$OH/CH$_3$COOH/H$_2$O 95:5:0.5:0.5). Yield: 4.89 g.

MS(ES$^+$): m/e=462.2(20%), 460.2 (40%).

3) Ethyl (2S)-2-(naphthalene-1-sulfonylamino)-3-{6-[4-(5,6,7,8-tetrahydro-[1,8]naphthyridin-2-yl)piperidin-1-yl]purin-9-yl}propionate

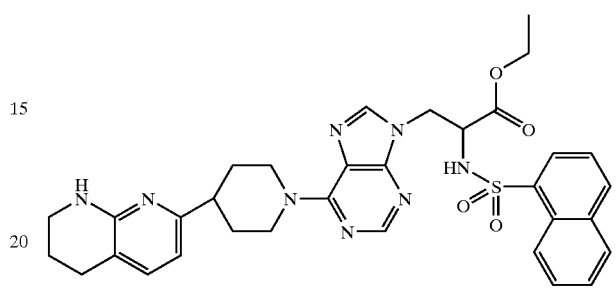

3.21 g of ethyl (2S)-3-(6-chloropurin-9-yl)-2-(naphthalene-1-sulfonylamino)propionate (Example 2) in 20 ml of abs. DMF were treated with 4.0 g of 7-(piperidin-4-yl)-1,2,3,4-tetrahydro-[1,8]naphthyridine and 3.88 g of diisopropylethylamine, and the mixture was stirred at 70° C. for 3 h. The solvent was distilled off in vacuo, the residue was taken up in EA and the mixture was extracted three times with water. The aqueous phases were extracted three times with DCM. The combined organic phases were dried over MgSO$_4$ and filtered, and the solvent was distilled off in vacuo. For purification, the residue was chromatographed over silica gel (DCM/CH$_3$OH/CH$_3$COOH/H$_2$O 95:5:0.5:0.5). Yield: 3.29 g.

MS(ES$^+$): m/e=641.4 (50%), 321.4 (100%).

4) tert-Butyl (2S)-2-benzyloxycarbonylamino-3-(6-chloropurin-9-yl)propionate

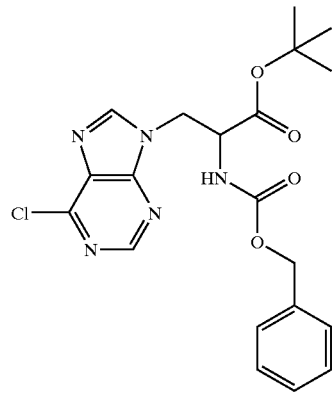

4a) tert-Butyl (2S)-3-(6-chloro-5-nitro-4-pyrimidin-4-ylamino)-2-benzyloxycarbonylaminopropionate 8.9 g (30.2 mmol) of tert-butyl (2S)-3-amino-2-benzyloxycarbonylaminopropionate were dissolved in 300 ml of abs. THF and treated at −10° C. with 6.15 g (31.8 mmol) of 4,6-dichloro-5-nitropyrimidine and 4.4 ml (31.8 mmol) of triethylamine. The cooling bath was removed and the reaction mixture reached room temperature after 30 minutes. The mixture was stirred for a further 12 h. The solvent was distilled off in vacuo, the residue was partitioned between EA and a saturated aqueous NaCl solution, the organic phase was dried over MgSO$_4$ and filtered, and the solvent was distilled off in vacuo. For purification, the residue was chromatographed over silica gel (EA/heptane 3:7). Yield: 11.27 g.

$^1$H-NMR (200 MHz, CDCl$_3$): 1.48 (s, 9H), 3.81–4.00 (m, 1H), 4.02–4.58 (m, 1H), 4.42–4.58 (m, 1H), 5.11 (s, 2H), 5.56 (d, broad, 1H), 7.36 (s, 5H), 7.80 (s, broad, 1H), 8.32 (s, 1H) ppm.

4b) tert-Butyl (2S)-3-(6-chloro-5-aminopyrimidin-4-ylamino)-2-benzyloxycarbonylaminopropionate 9.0 g of the compound of Example 4a) in 40 ml of ethanol were treated with 18.96 g of SnCl$_2$ and the reaction mixture was stirred at 70° C. for 30 minutes under nitrogen. The reaction solution was poured onto 40 g 9 of ice, 150 ml of EA and 25 g of Na$_2$CO$_3$ were added and the mixture was stirred for 15 min. It was then filtered, the aqueous phase was extracted a further two times with EA, the combined organic phases were washed with a saturated NaCl solution, dried over MgSO$_4$ and filtered, and the solvent was distilled off in vacuo. Yield: 6.73 g.

MS(ES$^+$): m/e=424.3 (35%), 422.3 (100%).

4c) tert-Butyl (2S)-2-benzyloxycarbonylamino-3-(6-chloropurin-9-yl)propionate 8.46 g of the compound of Example 4b) were dissolved in 50 ml of triethyl orthoformate and treated with 279 mg of ethanesulfonic acid. The mixture was stirred at room temperature for 12 h. The reaction mixture was diluted with 750 ml of EA and extracted three times with NaHCO$_3$ solution and washed twice with a saturated aqueous NaCl solution. The organic phase was dried over MgSO$_4$ and filtered, and the solvent was distilled off in vacuo. For purification, the residue was chromatographed over silica gel (EA/heptane 1:1). Yield: 6.64 g.

MS(ES$^+$): m/e=434.3 (35%), 432.3 (100%).

5) tert-Butyl (2S)-2-benzyloxycarbonylamino-3-{6-[4-(1,4,5,6-tetrahydropyrimidin-2-ylcarbamoyl)piperidin-1-yl]purin-9-yl}propionate

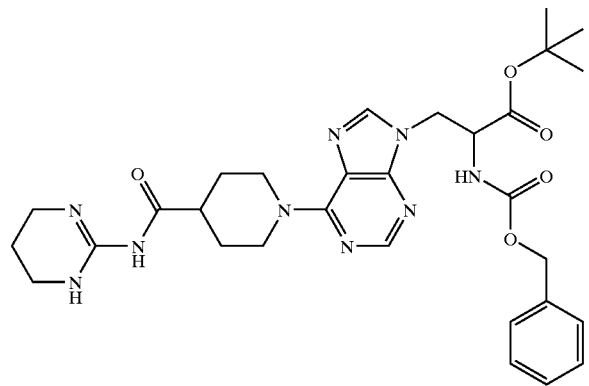

65 g (150.5 mmol) of tert-butyl (2S)-2-benzyloxycarbonylamino-3-(6-chloropurin-9-yl)propionate (Example 4) were dissolved in 350 ml of anhydrous THF, 100 ml of anhydrous triethylamine were added and then 74 g (168.8 mmol) of piperidine-4-carboxylic acid (1,4,5,6-tetrahydropyrimidin-2-yl)amide bistrifluoroacetate (Example 1) were introduced with stirring at room temperature and the mixture was stirred at 50° C. for approximately 8 h. After evaporation of the solvent in vacuo, a brown oil remained which was purified by chromatography over silica gel (eluent: EA, then EA/methanol 10:1). Yield: 86.5 g (95%) of slightly yellowish-foam.

MS(ES$^+$): m/e=606 (85%, M+H$^+$), 304 (100%).

$^1$H-NMR (400 MHz, DMSO): 1.3 (s, 9H), 1.55 (q, 1H), 1.85 (m, 1H), 1.95 (m, 1H), 2.8 (m, 1H), 3.2 (m, 1H), 3.35 (m, 2H), 4.45 (m, 1H), 4.5–4.6 (2m, 2H), 5.0 (s, 2H), 5.25–5.45 (bs, 2H), 7.25–7.4 (sh, 5H), 7.9 (d, 1H), 8.1 (s, 1H), 8.25 (s, 1H), 9.0 (s, 2H) ppm.

What is claimed is:

1. A process for the preparation of a compound of the formula (IV)

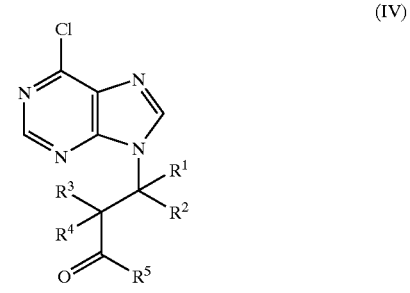

(IV)

wherein

R$^1$, R$^2$, R$^3$, R$^4$ independently are selected from the group consisting of hydrogen, fluorine, chlorine, —CN, (C$_1$–C$_{14}$)-alkyl, (C$_3$–C$_{14}$)-cycloalkyl, (C$_3$–C$_{14}$)-cycloalkyl-(C$_1$–C$_8$)-alkyl-, (C$_5$–C$_{14}$)-aryl, (C$_5$–C$_{14}$)-aryl-(C$_1$–C$_8$)-alkyl-, R$^6$—O—R$^7$, R$^6$R$^{6'}$N—R$^7$, R$^6$C(O)R$^7$, R$^6$S(O)$_2$N(R$^9$)R$^7$, R$^6$OC(O)N(R$^9$)R$^7$, R$^6$C(O)N(R$^5$)R$^7$, R$^6$N(R)C(O)N(R$^9$)R$^7$, R$^6$N(R$^9$)S(O)$_2$N(R$^9$)R$^7$, R$^6$S(O)$_2$ R$^7$, R$^6$SC(O)N(R$^9$)R$^7$, R$^6$N(R$^9$)C(O)R$^7$, R$^6$N(R$^9$)S(O)$_2$R$^7$, R$^6$N(R$^9$)R$^7$ and a 3-membered to 7-membered, saturated or unsaturated ring optionally containing one or two heteroatoms selected from the group consisting of nitrogen, sulfur and oxygen and which can be unsubstituted or mono- or disubstituted by a member selected from the group consisting of =O, =S, and R$^8$, where alkyl, cycloalkyl and aryl are unsubstituted or substituted by at least one member selected from the group consisting of fluorine, chlorine, bromine, —CF$_3$, —CN, R$^6$N(R$^9$)R$^7$, R$^6$R$^{6'}$NR$^7$, R$^6$C(O)R$^7$, R$^6$N(R$^9$)C(O)R$^7$, R$^6$N(R$^9$)S(O)$_2$R$^7$ and R$^6$, R$^6$—O—R$^7$;

R$^5$ is selected from the group consisting of hydroxyl, (C$_1$–C$_8$)-alkoxy, (C$_5$–C$_{14}$)-aryl-(C$_1$–C$_8$)-alkoxy-, (C$_1$–C$_8$)-alkylcarbonyloxy-(C$_1$–C$_4$)-alkoxy-, (C$_3$–C$_{14}$)-cycloalkoxy and (C$_3$–C$_{14}$)-cycloalkyl-(C$_1$–C$_8$)-alkoxy-;

R$^6$, R$^{6'}$ independently are selected from the group consisting of (C$_1$–C$_{18}$)-alkyl, (C$_3$–C$_{14}$)-cycloalkyl, (C$_3$–C$_{14}$)-cycloalkyl-(C$_1$–C$_8$)-alkyl-, (C$_5$–C$_{14}$)-aryl, (C$_5$–C$_{14}$)-aryl-(C$_1$–C$_8$)-alkyl- and a 3-membered to 7-membered, saturated or unsaturated ring containing one or two heteroatoms, selected from the group consisting of nitrogen, sulfur and oxygen, and is unsubstituted or mono- or disubstituted by a member selected from the group consisting of =O, =S, and $R^8$, where aryl, cycloalkyl and alkyl are optionally substituted once, twice or three times by a member selected from the group consisting of fluorine, chlorine, bromine, -cyano, —$CF_3$, nitro, carboxyl, $(C_1-C_6)$-alkyl, $(C_1-C_6)$-alkoxy, $(C_5-C_{14})$-aryl, $(C_1-C_6)$-alkoxy-$(C_1-C_6)$-alkyl-, $(C_1-C_6)$-alkoxycarbonyl, $(C_1-C_6)$-alkylcarbonyl, $(C_1-C_6)$-alkylaminocarbonyl, $(C_1-C_6)$-alkoxy-$(C_1-C_6)$-alkoxy-, $(C_5-C_{14})$-aryl-$(C_1-C_6)$-alkylcarbonyl, $(C_1-C_6)$-alkanoylamino, $(C_5-C_{14})$-arylsulfonylamino, $(C_1-C_6)$-alkylsulfonylamino, $(C_1-C_6)$-alkylamino, di-(($C_1-C_6)$-alkyl)amino, $(C_1-C_6)$-alkylsulfonyl, $(C_1-C_6)$alkylaminosulfonyl, $(C_6-C_{14})$-aryl-$(C_1-C_6)$-alkylaminosulfonyl and $(C_5-C_{14})$-aryl-$(C_1-C_6)$-alkylsulfonyl;

$R^7$ are independently $(C_1-C_4)$-alkanediyl or a direct bond;

$R^8$ is selected from the group consisting of $(C_1-C_{14})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, fluorine, chlorine, bromine, cyano, $CF_3$, nitro, carboxyl, $(C_1-C_6)$-alkoxy, $(C_1-C_6)$-alkoxy-$(C_1-C_6)$-alkyl-, $(C_1-C_6)$-alkoxycarbonyl, $(C_1-C_6)$-alkylcarbonyl, $(C_1-C_6)$-alkylaminocarbonyl, $(C_1-C_6)$-alkoxy-$(C_1-C_6)$-alkoxy-, $(C_5-C_{14})$-aryl-$(C_1-C_6)$-alkylcarbonyl, $(C_1-C_6)$-alkanoylamino, $(C_5-C_{14})$-arylsulfonylamino, $(C_1-C_6)$-alkylsulfonylamino, $(C_1-C_6)$-alkylamino, di-$(C_1-C_6)$-alkylamino, $(C_1-C_6)$-alkylsulfonyl, $(C_1-C_6)$-alkylaminosulfonyl, $(C_6-C_{14})$-aryl-$(C_1-C_6)$-alkylaminosulfonyl and $(C_5-C_{14})$-aryl-$(C_1-C_6)$-alkylsulfonyl; and $R^9$ is hydrogen or $(C_1-C_{14})$-alkyl;

in all its stereoisomeric forms admixtures thereof and its salts, comprising reacting the 5-nitropyrimidine of formula (V) with a primary amine of the formula (VI) to obtain a compound of the formula (VII),

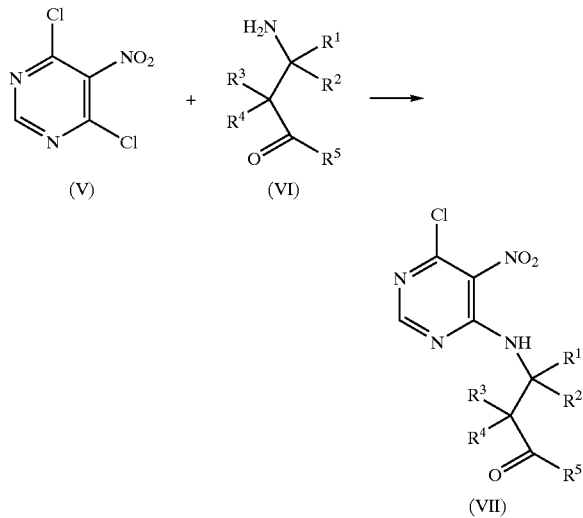

wherein $R^1$, $R^2$, $R^3$, $R^4$ and $R^5$ are defined as above, reducing the compound of formula (VII) to a compound of the formula

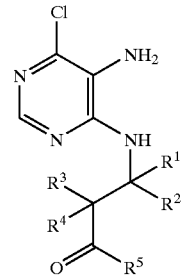

and cyclizing the compound of formula (VIII) to obtain a compound of formula (IV) by means of a tri($C_1-C_4$) alkyl orthoformate.

2. The process of claim 1, wherein $R^1$, $R^2$, $R^3$, $R^4$ independently are selected from the group consisting of hydrogen, $(C_1-C_{14})$-alkyl, $(C_3-C_{1-4})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $R^6R^{6'}N-R^7$, $R^6S(O)_2N(R^9)R^7$, $R^6N(R^9)S(O)_2N(R)R^7$, $R^6OC(O)N(R^9)R^7$, $R^6C(O)N(R^9)R^7$, $R^6N(R^9)R^7$ and a 3-membered to 7-membered, saturated or unsaturated ring containing one or two heteroatoms selected from the group consisting of nitrogen, sulfur and oxygen and optionally mono- or disubstituted by a member selected from the group consisting of =O, =S and $R^8$, where alkyl, cycloalkyl and aryl can be mono- or polysubstituted by a member selected from the group consisting of fluorine, chlorine, bromine, —$CF_3$, —CN and $R^6$—O—$R^7$;

$R^5$ is hydroxyl or $(C_1-C_{14})$-alkoxy;

$R^6$, $R^{6'}$ independently are selected from the group consisting of $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl- and a 3-membered to 7-membered, saturated or unsaturated ring, containing one or two heteroatoms selected from the group consisting of nitrogen, sulfur and oxygen and optionally mono- or disubstituted by a member selected from the group consisting of =O, =S, and $R^8$, where aryl, cycloalkyl and alkyl optionally are mono- to trisubstituted by a member selected from the group consisting of fluorine, chlorine, bromine, cyano, —$CF_3$, $(C_1-C_6)$-alkyl, $(C_1-C_6)$-alkoxy, $(C_5-C_{14})$-aryl, $(C_1-C_6)$-alkoxy-$(C_1-C_6)$-alkyl-, $(C_1-C_6)$-alkoxycarbonyl, and $(C_1-C_6)$-alkylcarbonyl;

$R^7$ independently is $(C_1-C_{14})$-alkylene or a direct bond;

$R^8$ is selected from the group consisting of $(C_1-C_{14})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, fluorine, chlorine, bromine, $CF_3$, $(C_1-C_6)$-alkoxy and $(C_1-C_6)$-alkoxy-$(C_1-C_6)$-alkyl-; and $R^9$ is hydrogen or $(C_1-C_4)$-alkyl.

3. The process of claim 1 wherein $R^1$, $R^2$, $R^3$, $R^4$ independently are selected from the group consisting of hydrogen, $R^6S(O)_2N(R^9)R^7$ and $R^6OC(O)N(R^9)R^7$;

$R^5$ is $(C_1-C_{14})$-alkoxy;

$R^6$ is $(C_5-C_{14})$-aryl or $(C_5-C_{14})$-aryl-$(C_1-C_8)$-alkyl;

$R^7$ is a direct bond; and $R^9$ is hydrogen.

4. A compound of the formula

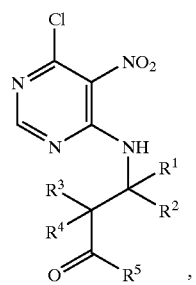

(VII)

wherein $R^1$, $R^2$, $R^3$, $R^4$ independently are selected from the group consisting of hydrogen, fluorine, chlorine, —CN, $(C_1–C_{14})$-alkyl, $(C_3–C_{14})$-cycloalkyl, $(C_3–C_{14})$-cycloalkyl-$(C_1–C_8)$-alkyl-, $(C_5–C_{14})$-aryl, $(C_5–C_{14})$-aryl-$(C_1–C_8)$-alkyl-, $R^6$—O—$R^7$, $R^6R^{6'}N$—$R^7$, $R^6C(O)R^7$, $R^6S(O)_2N(R^9)R^7$, $R^6OC(O)N(R)R^7$, $R^6C(O)N(R^5)R^7$, $R^6N(R^9)C(O)N(R^9)R^7$, $R^6N(R^9)S(O)_2N(R^9)R^7$, $R^6S(O)_2R^7$, $R^6SC(O)N(R^9)R^7$, $R^6N(R^9)C(O)R^7$, $R^6N(R^9)S(O)_2R^7$, $R^6N(R)R^7$ and a 3-membered to 7-membered, saturated or unsaturated ring optionally containing one or two heteroatoms selected from the group consisting of nitrogen, sulfur and oxygen and which can be unsubstituted or mono- or disubstituted by a member selected from the group consisting of =O, =S, and $R^8$, where alkyl, cycloalkyl and aryl are unsubstituted or substituted by at least one member selected from the group consisting of fluorine, chlorine, bromine, —$CF_3$, —CN, $R^6N(R^9)R^7$, $R^6R^6NR^7$, $R^6C(O)R^7$, $R^6N(R^9)C(O)R^7$, $R^6N(R^9)S(O)_2R^7$ and $R^6$, $R^6$—O—$R^7$;

$R^5$ is selected from the group consisting of hydroxyl, $(C_1–C_8)$-alkoxy, $(C_5–C_{14})$-aryl-$(C_1–C_8)$-alkoxy-, $(C_1–C_8)$-alkylcarbonyloxy-$(C_1–C_4)$-alkoxy-, $(C_3–C_{14})$-cycloalkoxy and $(C_3–C_{14})$-cycloalkyl-$(C_1–C_8)$-alkoxy-;

$R^6$, $R^{6'}$ independently are selected from the group consisting of $(C_1–C_{18})$-alkyl, $(C_3–C_{14})$-cycloalkyl, $(C_3–C_{14})$-cycloalkyl-$(C_1–C_8)$-alkyl-, $(C_5–C_{14})$-aryl, $(C_5–C_{14})$-aryl-$(C_1–C_8)$-alkyl- and a 3-membered to 7-membered, saturated or unsaturated ring containing one or two heteroatoms, selected from the group consisting of nitrogen, sulfur and oxygen, and is unsubstituted or mono- or disubstituted by a member selected from the group consisting of =O, =S, and $R^8$, where aryl, cycloalkyl and alkyl are optionally substituted once, twice or three times by a member selected from the group consisting of fluorine, chlorine, bromine, -cyano, —$CF_3$, nitro, carboxyl, $(C_1–C_6)$-alkyl, $(C_1–C_6)$-alkoxy, $(C_5–C_{14})$-aryl, $(C_1–C_6)$-alkoxy-$(C_1–C_6)$-alkyl-, $(C_1–C_6)$-alkoxycarbonyl, $(C_1–C_6)$-alkylcarbonyl, $(C_1–C_6)$-alkylaminocarbonyl, $(C_1–C_6)$-alkoxy-$(C_1–C_6)$-alkoxy-, $(C_5–C_{14})$-aryl-$(C_1–C_6)$-alkylcarbonyl, $(C_1–C_6)$-alkanoylamino, $(C_5–C_{14})$-arylsulfonylamino, $(C_1–C_6)$-alkylsulfonylamino, $(C_1–C_6)$-alkylamino, di-$((C_1–C_6)$-alkyl)amino, $(C_1–C_6)$-alkylsulfonyl, $(C_1–C_6)$-alkylaminosulfonyl, $(C_6–C_{14})$-aryl-$(C_1–C_6)$-alkylaminosulfonyl and $(C_5–C_{14})$-aryl-$(C_1–C_6)$-alkylsulfonyl;

$R^7$ are independently $(C_1–C_4)$-alkanediyl or a direct bond;

$R^8$ is selected from the group consisting of $(C_1–C_{14})$-alkyl, $(C_3–C_{14})$-cycloalkyl, $(C_3–C_{14})$-cycloalkyl-$(C_1–C_8)$-alkyl-, $(C_5–C_{14})$-aryl, $(C_5–C_{14})$-aryl-$(C_1–C_8)$-alkyl-, fluorine, chlorine, bromine, cyano, $CF_3$, nitro, carboxyl, $(C_1–C_6)$-alkoxy, $(C_1–C_6)$-alkoxy-$(C_1–C_6)$-alkyl-, $(C_1–C_6)$-alkoxycarbonyl, $(C_1–C_6)$-alkylcarbonyl, $(C_1–C_6)$-alkylaminocarbonyl, $(C_1–C_6)$-alkoxy-$(C_1–C_6)$-alkoxy-, $(C_5–C_{14})$-aryl-$(C_1–C_6)$-alkylcarbonyl, $(C_1–C_6)$-alkanoylamino, $(C_5–C_{14})$-arylsulfonylamino, $(C_1–C_6)$-alkylsulfonylamino, $(C_1–C_6)$-alkylamino, di-$(C_1–C_6)$-alkylamino, $(C_1–C_6)$-alkylsulfonyl, $(C_1–C_6)$-alkylaminosulfonyl, $(C_6–C_{14})$-aryl-$(C_1–C_6)$-alkylaminosulfonyl and $(C_5–C_{14})$-aryl-$(C_1–C_6)$-alkylsulfonyl; and $R^9$ is hydrogen or $(C_1–C_{14})$-alkyl;

in all its stereoisomeric forms and mixtures thereof and its salts.

5. A compound of the formula

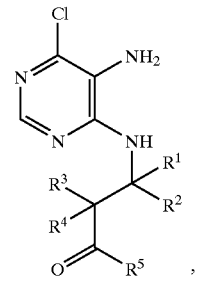

(VIII)

wherein $R^1$, $R^2$, $R^3$, $R^4$ independently are selected from the group consisting of hydrogen, fluorine, chlorine, —CN, $(C_1–C_{14})$-alkyl, $(C_3–C_{14})$-cycloalkyl, $(C_3–C_{14})$-cycloalkyl-$(C_1–C_8)$-alkyl-, $(C_5–C_{14})$-aryl, $(C_5–C_{14})$-aryl-$(C_1–C_8)$-alkyl-, $R^6$—O—$R^7$, $R^6R^{6'}N$—$R^7$, $R^6C(O)R^7$, $R^6S(O)_2N(R^9)R^7$, $R^6OC(O)N(R^9)R^7$, $R^6C(O)N(R^5)R^7$, $R^6N(R^9)C(O)N(R^9)R^7$, $R^6N(R^9)S(O)_2N(R^9)R^7$, $R^6S(O)_2R^7$, $R^6SC(O)N(R)R^7$, $R^6N(R^9)C(O)R^7$, $R^6N(R^9)S(O)_2R^7$, $R^6N(R^9)R^7$ and a 3-membered to 7-membered, saturated or unsaturated ring optionally containing one or two heteroatoms selected from the group consisting of nitrogen, sulfur and oxygen and which can be unsubstituted or mono- or disubstituted by a member selected from the group consisting of =O, =S, and $R^8$, where alkyl, cycloalkyl and aryl are unsubstituted or substituted by at least one member selected from the group consisting of fluorine, chlorine, bromine, —$CF_3$, —CN, $R^6N(R^9)R^1$, $R^6R^6NR^7$, $R^6C(O)R^7$, $R^6N(R^9)C(O)R^7$, $R^6N(R^9)S(O)_2R^7$ and $R^6$, $R^6$—O—$R^7$;

$R^5$ is selected from the group consisting of hydroxyl, $(C_1–C_8)$-alkoxy, $(C_5–C_{14})$-aryl-$(C_1–C_8)$-alkoxy-, $(C_1–C_8)$-alkylcarbonyloxy-$(C_1–C_4)$-alkoxy-, $(C_3–C_{14})$-cycloalkoxy and $(C_3–C_{1-4})$-cycloalkyl-$(C_1–C_8)$-alkoxy-;

$R^6$, $R^{6'}$ independently are selected from the group consisting of $(C_1–C_{18})$-alkyl, $(C_3–C_{14})$-cycloalkyl, $(C_3–C_{14})$-cycloalkyl-$(C_1–C_8)$-alkyl-, $(C_5–C_{14})$-aryl, $(C_5–C_{14})$-aryl-$(C_1–C_8)$-alkyl- and a 3-membered to 7-membered, saturated or unsaturated ring containing one or two heteroatoms, selected from the group consisting of nitrogen, sulfur and oxygen, and is unsubstituted or mono- or disubstituted by a member selected from the group consisting of =O, =S, and $R^8$, where aryl, cycloalkyl and alkyl are optionally substituted once, twice or three times by a member selected from the group consisting of fluorine, chlorine, bromine, -cyano, —$CF_3$, nitro, carboxyl, $(C_1–C_6)$-alkyl, ($C_1$–$C_6$)-alkoxy, ($C_5$–$C_{14}$)-aryl, ($C_1$–$C_6$)-alkoxy-($C_1$–$C_6$)-alkyl-, ($C_1$–$C_6$)-alkoxycarbonyl, ($C_1$–$C_6$)-alkylcarbonyl, ($C_1$–$C_6$)-alkylaminocarbonyl, ($C_1$–$C_6$)-alkoxy-($C_1$–$C_6$)-alkoxy-, ($C_5$–$C_{14}$)-aryl-($C_1$–$C_6$)-alkylcarbonyl, ($C_1$–$C_6$)-alkanoylamino, ($C_5$–$C_{14}$)-arylsulfonylamino, ($C_1$–$C_6$)-alkylsulfonylamino, ($C_1$–$C_6$)-alkylamino, di-(($C_1$–$C_6$)-alkyl)amino, ($C_1$–$C_6$)-alkylsulfonyl, ($C_1$–$C_6$)-alkylaminosulfonyl, ($C_6$–$C_{14}$)-aryl-($C_1$–$C_6$)-alkylaminosulfonyl and ($C_5$–$C_{14}$)-aryl-($C_1$–$C_6$)-alkylsulfonyl;

$R^7$ are independently ($C_1$–$C_4$)-alkanediyl or a direct bond;

$R^8$ is selected from the group consisting of ($C_1$–$C_{14}$)-alkyl, ($C_3$–$C_{14}$)-cycloalkyl, ($C_3$–$C_{14}$)-cycloalkyl-($C_1$–$C_8$)-alkyl-, ($C_5$–$C_{14}$)-aryl, ($C_5$–$C_{14}$)-aryl-($C_1$–$C_8$)-alkyl-, fluorine, chlorine, bromine, cyano, $CF_3$, nitro, carboxyl, ($C_1$–$C_6$)-alkoxy, ($C_1$–$C_6$)-alkoxy-($C_1$–$C_6$)-alkyl-, ($C_1$–$C_6$)-alkoxycarbonyl, ($C_1$–$C_6$)-alkylcarbonyl, ($C_1$–$C_6$)-alkylaminocarbonyl, ($C_1$–$C_6$)-alkoxy-($C_1$–$C_6$)-alkoxy-, ($C_5$–$C_{14}$)-aryl-($C_1$–$C_6$)-alkylcarbonyl, ($C_1$–$C_6$)-alkanoylamino, ($C_5$–$C_{14}$)-arylsulfonylamino, ($C_1$–$C_6$)-alkylsulfonylamino, ($C_1$–$C_6$)-alkylamino, di-($C_1$–$C_6$)-alkylamino, ($C_1$–$C_6$)-alkylsulfonyl, ($C_1$–$C_6$)-alkylaminosulfonyl, ($C_6$–$C_{14}$)-aryl-($C_1$–$C_6$)-alkylaminosulfonyl and ($C_5$–$C_{14}$)-aryl-($C_1$–$C_6$)-alkylsulfonyl; and $R^9$ is hydrogen or ($C_1$–$C_{14}$)-alkyl; in all its stereoisomeric forms and mixtures thereof and its salts.

6. A process for the preparation of a compound of the formula

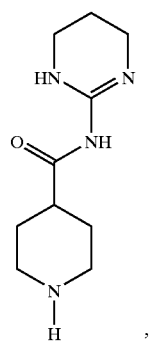

(IX-A)

and its salts, comprising reacting a compound of formula (X) with 2-aminopyrimidine of formula (XI) to obtain a compound of formula (XII),

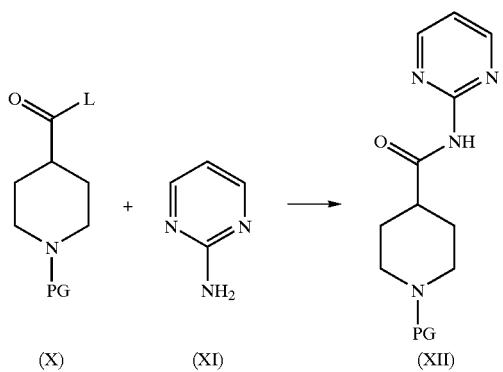

where PG is an amino protective group and L is a nucleophilically substitutable leaving group, and reducing the compound of formula (XII) to obtain a compound of the formula

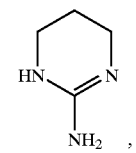

(XIV)

or reacting a compound of formula (X) with 2-amino-1,4,5,6-tetrahydropyrimidine of the formula

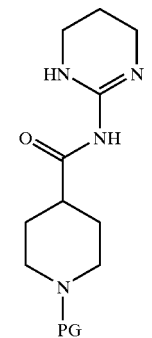

(XIII)

to give a compound of formula (XIII), and deprotecting the compound of the formula (XIII) to obtain the compound of the formula (IX-A).

7. The process of claim 6, wherein PG is tertbutoxycarbonyl or benzyloxycarbonyl.

8. The process of claim 6 wherein L is pentafluorophenoxy.

9. A compound of the formula

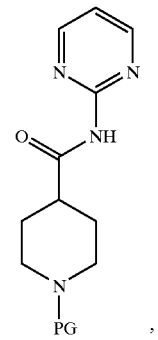

(XII)

wherein PG is an amino protective group, and its salts.

10. A compound of the formula

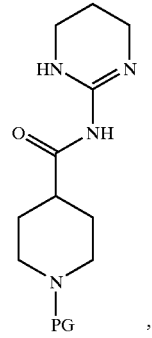

(XIII)

wherein PG is an amino protective group, and its salts.

11. A compound of the formula

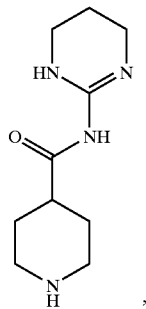

(IX-A)

and its salts.

12. A process for the preparation of a compound of the formula

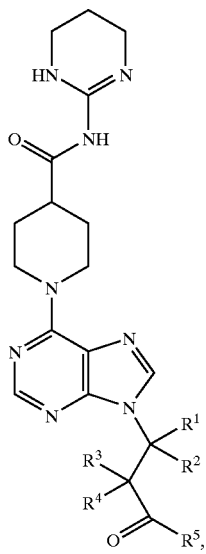

(I-A)

wherein $R^1$, $R^2$, $R^3$, $R^4$ independently are selected from the group consisting of hydrogen, fluorine, chlorine, —CN, $(C_1-C_{14})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $R^6$—O—$R^7$, $R^6R^{6'}N$—$R^7$, $R^6C(O)R^7$, $R^6S(O)_2N(R)R^7$, $R^6OC(O)N(R^9)R^7$, $R^6C(O)N(R^5)R^7$, $R^6N(R^9)C(O)N(R^9)R^7$, $R^6N(R^9)S(O)_2N(R^9)R^7$, $R^6S(O)_2R^7$, $R^6SC(O)N(R^9)R^7$, $R^6N(R^9)C(O)R^7$, $R^6N(R^9)S(O)_2R^7$, $R^6N(R^9)R^7$ and a 3-membered to 7-membered, saturated or unsaturated ring optionally containing one or two heteroatoms selected from the group consisting of nitrogen, sulfur and oxygen and which can be unsubstituted or mono- or disubstituted by a member selected from the group consisting of =O, =S, and $R^8$, where alkyl, cycloalkyl and aryl are unsubstituted or substituted by at least one member selected from the group consisting of fluorine, chlorine, bromine, —CF$_3$, —CN, $R^6N(R^9)R^7$, $R^6R^{6'}NR^7$, $R^6C(O)R^7$, $R^6N(R^9)C(O)R^7$, $R^6N(R^9)S(O)_2R^7$ and $R^6$, $R^6$—O—$R^7$;

$R^5$ is selected from the group consisting of hydroxyl, $(C_1-C_8)$-alkoxy, $(C_5-C_{14})$-aryl-$(C_1-C_8)$-alkoxy-, $(C_1-C_8)$-alkylcarbonyloxy-$(C_1-C_4)$-alkoxy-, $(C_3-C_{14})$-cycloalkoxy and $(C_3-C_{14})$-cycloalkyl-$(C_1-C_8)$-alkoxy-;

$R^6$, $R^{6'}$ independently are selected from the group consisting of $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl- and a 3-membered to 7-membered, saturated or unsaturated ring containing one or two heteroatoms, selected from the group consisting of nitrogen, sulfur and oxygen, and is unsubstituted or mono- or disubstituted by a member selected from the group consisting of =O, =S, and $R^8$, where aryl, cycloalkyl and alkyl are optionally substituted once, twice or three times by a member selected from the group consisting of fluorine, chlorine, bromine, -cyano, —CF$_3$, nitro, carboxyl, $(C_1-C_6)$-alkyl, $(C_1-C_6)$-alkoxy, $(C_5-C_{14})$-aryl, $(C_1-C_6)$-alkoxy-$(C_1-C_6)$-alkyl-, $(C_1-C_6)$-alkoxycarbonyl, $(C_1-C_6)$-alkylcarbonyl, $(C_1-C_6)$-alkylaminocarbonyl, $(C_1-C_6)$-alkoxy-$(C_1-C_6)$-alkoxy-, $(C_5-C_{14})$-aryl-$(C_1-C_6)$-alkylcarbonyl, $(C_1-C_6)$-alkanoylamino, $(C_5-C_{14})$-arylsulfonylamino, $(C_1-C_6)$-alkylsulfonylamino, $(C_1-C_6)$-alkylamino, di-$((C_1-C_6)$-alkyl)amino, $(C_1-C_6)$-alkylsulfonyl, $(C_1-C_6)$-alkylaminosulfonyl, $(C_6-C_{14})$-aryl-$(C_1-C_6)$-alkylaminosulfonyl and $(C_5-C_{14})$-aryl-$(C_1-C_6)$-alkylsulfonyl;

$R^7$ are independently $(C_1-C_4)$-alkanediyl or a direct bond;

$R^8$ is selected from the group consisting of $(C_1-C_{14})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, fluorine, chlorine, bromine, cyano, CF$_3$, nitro, carboxyl, $(C_1-C_6)$-alkoxy, $(C_1-C_6)$-alkoxy-$(C_1-C_6)$-alkyl-, $(C_1-C_6)$-alkoxycarbonyl, $(C_1-C_6)$-alkylcarbonyl, $(C_1-C_6)$-alkylaminocarbonyl, $(C_1-C_6)$-alkoxy-$(C_1-C_6)$-alkoxy-, $(C_5-C_{14})$-aryl-$(C_1-C_6)$-alkylcarbonyl, $(C_1-C_6)$-alkanoylamino, $(C_5-C_{14})$-arylsulfonylamino, $(C_1-C_6)$-alkylsulfonylamino, $(C_1-C_6)$-alkylamino, di-$(C_1-C_6)$-alkylamino, $(C_1-C_6)$-alkylsulfonyl, $(C_1-C_6)$-alkylaminosulfonyl, $(C_6-C_{14})$-aryl-$(C_1-C_6)$-alkylaminosulfonyl and $(C_5-C_{14})$-aryl-$(C_1-C_6)$-alkylsulfonyl; and $R^9$ is hydrogen or $(C_1-C_{14})$-alkyl; in all its stereoisomeric forms and mixtures thereof and its salts, which comprises reacting a compound of the formula

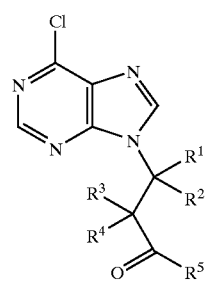

(IV)

with a compound of the formula

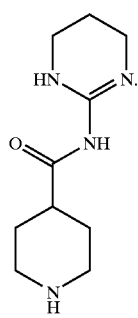

(IX-A)

13. A process for the preparation of a compound of the formula

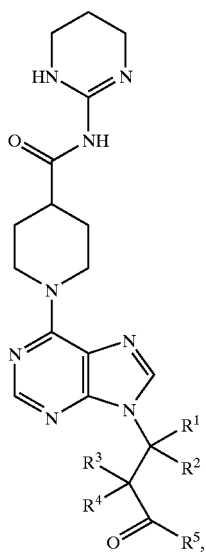

(I-A)

wherein $R^1$, $R^2$, $R^3$, $R^4$ independently are selected from the group consisting of hydrogen, fluorine, chlorine, —CN, $(C_1-C_{14})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $R^6$—O—$R^7$, $R^6R^{6'}N$—$R^7$, $R^6C(O)R^7$, $R^6S(O)_2N(R^9)R^7$, $R^6OC(O)N(R^9)R^7$, $R^6C(O)N(R^5)R^7$, $R^6N(R^9)C(O)N(R^9)R^7$, $R^6N(R^9)S(O)_2N(R^9)R^7$, $R^6S(O)_2R^7$, $R^6SC(O)N(R^9)R^7$, $R^6N(R^9)C(O)R^7$, $R^6N(R^9)S(O)_2R^7$, $R^6N(R^9)R^7$ and a 3-membered to 7-membered, saturated or unsaturated ring optionally containing one or two heteroatoms selected from the group consisting of nitrogen, sulfur and oxygen and which can be unsubstituted or mono- or disubstituted by a member selected from the group consisting of =O, =S, and $R^8$, where alkyl, cycloalkyl and aryl are unsubstituted or substituted by at least one member selected from the group consisting of fluorine, chlorine, bromine, —$CF_3$, —CN, $R^6N(R^9)R^7$, $R^1R^{6'}NR^7$, $R^6C(O)R^7$, $R^6N(R^9)C(O)R^7$, $R^6N(R^9)S(O)_2R^7$ and $R^6$, $R^6$—O—$R^7$;

$R^5$ is selected from the group consisting of hydroxyl, $(C_1-C_5)$-alkoxy, $(C_5-C_{14})$-aryl-$(C_1-C_8)$-alkoxy-, $(C_1-C_8)$-alkylcarbonyloxy-$(C_1-C_4)$-alkoxy-, $(C_3-C_{14})$-cycloalkoxy and $(C_3-C_{14})$-cycloalkyl-$(C_1-C_8)$-alkoxy-;

$R^6$, $R^{6'}$ independently are selected from the group consisting of $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl- and a 3-membered to 7-membered, saturated or unsaturated ring containing one or two heteroatoms, selected from the group consisting of nitrogen, sulfur and oxygen, and is unsubstituted or mono- or disubstituted by a member selected from the group consisting of =O, =S, and $R^8$, where aryl, cycloalkyl and alkyl are optionally substituted once, twice or three times by a member selected from the group consisting of fluorine, chlorine, bromine, -cyano, —$CF_3$, nitro, carboxyl, $(C_1-C_6)$-alkyl, $(C_1-C_6)$-alkoxy, $(C_5-C_{14})$-aryl, $(C_1-C_6)$-alkoxy-$(C_1-C_6)$-alkyl-, $(C_1-C_6)$-alkoxycarbonyl, $(C_1-C_6)$-alkylcarbonyl, $(C_1-C_6)$-alkylaminocarbonyl, $(C_1-C_6)$-alkoxy-$(C_1-C_6)$-alkoxy-, $(C_5-C_{14})$-aryl-$(C_1-C_6)$-alkylcarbonyl, $(C_1-C_6)$-alkanoylamino, $(C_5-C_{14})$-arylsulfonylamino, $(C_1-C_6)$-alkylsulfonylamino, $(C_1-C_6)$-alkylamino, di-$((C_1-C_6)$-alkyl)amino, $(C_1-C_6)$-alkylsulfonyl, $(C_1-C_6)$-alkylaminosulfonyl, $(C_6-C_{14})$-aryl-$(C_1-C_6)$-alkylaminosulfonyl and $(C_5-C_{14})$-aryl-$(C_1-C_6)$-alkylsulfonyl;

$R^7$ are independently $(C_1-C_4)$-alkanediyl or a direct bond;

$R^8$ is selected from the group consisting of $(C_1-C_{14})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, fluorine, chlorine, bromine, cyano, $CF_3$, nitro, carboxyl, $(C_1-C_6)$-alkoxy, $(C_1-C_6)$-alkoxy-$(C_1-C_6)$-alkyl-, $(C_1-C_6)$-alkoxycarbonyl, $(C_1-C_6)$-alkylcarbonyl, $(C_1-C_6)$-alkylaminocarbonyl, $(C_1-C_6)$-alkoxy-$(C_1-C_6)$-alkoxy-, $(C_5-C_{14})$-aryl-$(C_1-C_6)$-alkylcarbonyl, $(C_1-C_6)$-alkanoylamino, $(C_5-C_{14})$-arylsulfonylamino, $(C_1-C_6)$-alkylsulfonylamino, $(C_1-C_6)$-alkylamino, di-$(C_1-C_6)$-alkylamino, $(C_1-C_6)$-alkylsulfonyl, $(C_1-C_6)$-alkylaminosulfonyl, $(C_6-C_{14})$-aryl-$(C_1-C_6)$-alkylaminosulfonyl and $(C_5-C_{14})$-aryl-$(C_1-C_6)$-alkylsulfonyl; and $R^9$ is hydrogen or $(C_1-C_{14})$-alkyl; in all its stereoisomeric forms and mixtures thereof and its salts, comprising reacting a compound of the formula

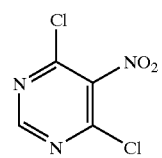

(V)

with a compound of the formula

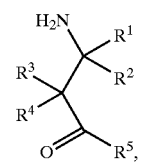

(VI)

to obtain a compound of the formula (VII)

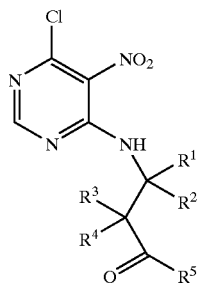

reducing the compound of formula (VII) to obtain a compound of the formula (VIII)

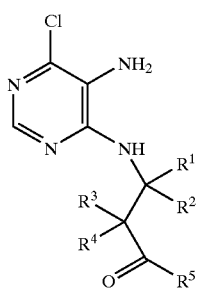

reacting the compound of formula (VIII) with a tri($C_1$–$C_4$) alkyl orthoformate to obtain a compound of the formula (IV)

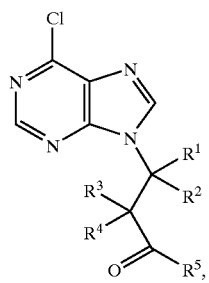

and reacting the compound of formula (IV) with a compound of the formula (IX-A)

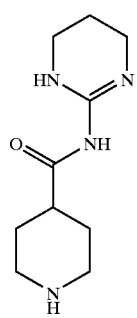

to obtain a compound of the formula (I-A)

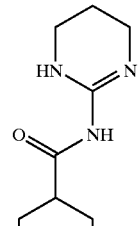

14. A process for the preparation of a compound of the formula (I-B)

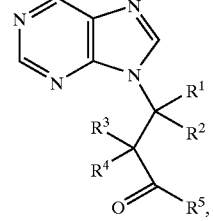

wherein the $R^1$, $R^2$, $R^3$, $R^4$ independently are selected from the group consisting of hydrogen, fluorine, chlorine, —CN, ($C_1$–$C_{14}$)-alkyl, ($C_3$–$C_{14}$)-cycloalkyl, ($C_3$–$C_{14}$)-cycloalkyl-($C_1$–$C_8$)-alkyl-, ($C_5$–$C_{14}$)-aryl, ($C_5$–$C_{14}$)-aryl-($C_1$–$C_8$)-alkyl-, $R^6$—O—$R^7$, $R^6R^6$'N—$R^7$, $R^6C(O)R^7$, $R^6S(O)_2N(R^9)R^7$, $R^6OC(O)N(R^9)R^7$, $R^6C(O)N(R^5)R^7$, $R^6N(R^9)C(O)N(R^9)R^7$, $R^6N(R^9)S(O)_2N(R^9)R^7$, $R^6S(O)_2R^7$, $R^6SC(O)N(R^9)R$ $R^6N(R^9)C(O)R^7$, $R^6N(R^9)S(O)_2R^7$, $R^6N(R^9)R^7$ and a 3-membered to 7-membered, saturated or unsaturated ring optionally containing one or two heteroatoms selected from the group consisting of nitrogen, sulfur and oxygen and which can be unsubstituted or mono- or disubstituted by a member selected from the group consisting of =O, =S, and $R^8$, where alkyl, cycloalkyl and aryl are unsubstituted or substituted by at least one member selected from the group consisting of fluorine, chlorine, bromine, —CF$_3$, —CN, R$^6$N(R$^9$)R$^7$, R$^6$R$^{6'}$NR$^7$, R$^6$C(O)R$^7$, R$^6$N(R$^9$)C(O)R$^7$, R$^6$N(R$^9$)S(O)$_2$R$^7$ and R$^6$, R$^6$—O—R$^7$;

R$^5$ is selected from the group consisting of hydroxyl, (C$_1$–C$_8$)-alkoxy, (C$_5$–C$_{14}$)-aryl-(C$_1$–C$_8$)-alkoxy-, (C$_1$–C$_8$)-alkylcarbonyloxy-(C$_1$–C$_4$)-alkoxy-, (C$_3$–C$_{14}$)-cycloalkoxy and (C$_3$–C$_{14}$)-cycloalkyl-(C$_1$–C$_8$)-alkoxy-;

R$^6$, R$^{6'}$ independently are selected from the group consisting of (C$_1$–C$_{18}$)-alkyl, (C$_3$–C$_{14}$)-cycloalkyl, (C$_3$–C$_{14}$)-cycloalkyl-(C$_1$–C$_8$)-alkyl-, (C$_5$–C$_{14}$)-aryl, (C$_5$–C$_{14}$)-aryl-(C$_1$–C$_8$)-alkyl- and a 3-membered to 7-membered, saturated or unsaturated ring containing one or two heteroatoms, selected from the group consisting of nitrogen, sulfur and oxygen, and is unsubstituted or mono- or disubstituted by a member selected from the group consisting of =O, =S, and R$^8$, where aryl, cycloalkyl and alkyl are optionally substituted once, twice or three times by a member selected from the group consisting of fluorine, chlorine, bromine, -cyano, —CF$_3$, nitro, carboxyl, (C$_1$–C$_6$)-alkyl, (C$_1$–C$_6$)-alkoxy, (C$_5$–C$_{14}$)-aryl, (C$_1$–C$_6$)-alkoxy-(C$_1$–C$_6$)-alkyl-, (C$_1$–C$_6$)-alkoxycarbonyl, (C$_1$–C$_6$)-alkylcarbonyl, (C$_1$–C$_6$)-alkylaminocarbonyl, (C$_1$–C$_6$)-alkoxy-(C$_1$–C$_6$)-alkoxy-, (C$_5$–C$_{14}$)-aryl-(C$_1$–C$_6$)-alkylcarbonyl, (C$_1$–C$_6$)-alkanoylamino, (C$_5$–C$_{14}$)-arylsulfonylamino, (C$_1$–C$_6$)-alkylsulfonylamino, (C$_1$–C$_6$)-alkylamino, di-((C$_1$–C$_6$)-alkyl)amino, (C$_1$–C$_6$)-alkylsulfonyl, (C$_1$–C$_6$)-alkylaminosulfonyl, (C$_6$–C$_{14}$)-aryl-(C$_1$–C$_6$)-alkylaminosulfonyl and (C$_5$–C$_{14}$)-aryl-(C$_1$–C$_6$)-alkylsulfonyl;

R$^7$ are independently (C$_1$–C$_4$)-alkanediyl or a direct bond;

R$^8$ is selected from the group consisting of (C$_1$–C$_{14}$)-alkyl, (C$_3$–C$_{14}$)-cycloalkyl, (C$_3$–C$_{14}$)cycloalkyl-(C$_1$–C$_8$)-alkyl-, (C$_5$–C$_{14}$)-aryl, (C$_5$–C$_{14}$)-aryl-(C$_1$–C$_8$)-alkyl-, fluorine, chlorine, bromine, cyano, CF$_3$, nitro, carboxyl, (C$_1$–C$_6$)-alkoxy, (C$_1$–C$_6$)-alkoxy-(C$_1$–C$_6$)-alkyl-, (C$_1$–C$_6$)-alkoxycarbonyl, (C$_1$–C$_6$)-alkylcarbonyl, (C$_1$–C$_6$)-alkylaminocarbonyl, (C$_1$–C$_6$)-alkoxy-(C$_1$–C$_6$)-alkoxy-, (C$_5$–C$_{14}$)-aryl-(C$_1$–C$_6$)-alkylcarbonyl, (C$_1$–C$_6$)-alkanoylamino, (C$_5$–C$_{14}$)-arylsulfonylamino, (C$_1$–C$_6$)-alkylsulfonylamino, (C$_1$–C$_6$)-alkylamino, di-(C$_1$–C$_6$)-alkylamino, (C$_1$–C$_6$)-alkylsulfonyl, (C$_1$–C$_6$)-alkylaminosulfonyl, (C$_6$–C$_{14}$)-aryl-(C$_1$–C$_6$)-alkylaminosulfonyl and (C$_5$–C$_{14}$)-aryl-(C$_1$–C$_6$)-alkylsulfonyl; and R$^9$ is hydrogen or (C$_1$–C$_{14}$)-alkyl; in all its stereoisomeric forms and mixtures thereof and its salts, comprising reacting a compound of the formula

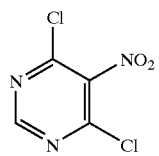

(V)

with a compound of the formula

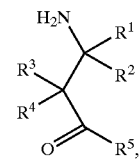

(VI)

reducing the compound of formula

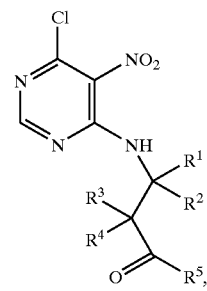

(VII)

to obtain a compound of the formula

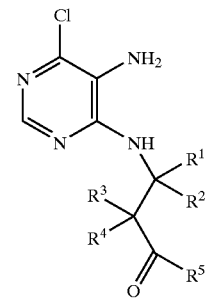

(VIII)

reacting the compound of formula (VIII) with a tri(C$_1$–C$_4$) alkyl orthoformate to obtain a compound of the formula

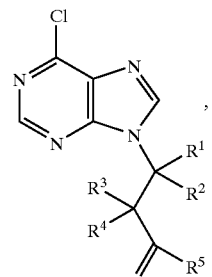

(IV)

and reacting the compound of formula (IV) with a compound of the formula

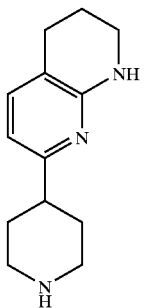
(IX-B)

to obtain a compound of the formula

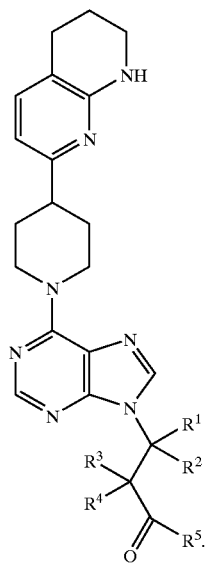
(I-B)

15. A process for the preparation of a compound of the formula

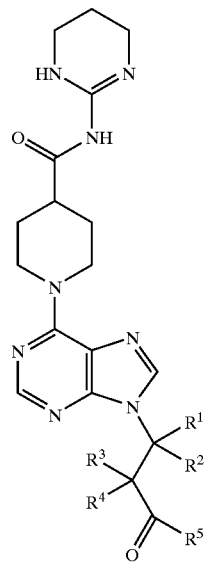
(I-A)

wherein $R^1$, $R^2$, $R^3$, $R^4$ independently are selected from the group consisting of hydrogen, fluorine, chlorine, —CN, $(C_1-C_4)$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $R^6$—O—$R^7$, $R^6R^{6'}N$—$R^7$, $R^6C(O)R^7$, $R^6S(O)_2N(R^9)R^7$, $R^6OC(O)N(R^9)R^7$, $R^6C(O)N(R^5)R^7$, $R^6N(R^9)C(O)N(R^9)R^7$, $R^6N(R^9)S(O)_2N(R^9)R^7$, $R^6S(O)_2R^7$, $R^6SC(O)N(R^9)R^7$, $R^6N(R^9)C(O)R^7$, $R^6N(R^9)S(O)_2R^7$, $R^6N(R^9)R^7$ and a 3-membered to 7 membered, saturated or unsaturated ring optionally containing one or two heteroatoms selected from the group consisting of nitrogen, sulfur and oxygen and which can be unsubstituted or mono- or disubstituted by a member selected from the group consisting of =O, =S, and $R^8$, where alkyl, cycloalkyl and aryl are unsubstituted or substituted by at least one member selected from the group consisting of fluorine, chlorine, bromine, —$CF_3$, —CN, $R^6N(R^9)R^7$, $R^6R^{6'}NR^7$, $R^6C(O)R^7$, $R^6N(R^9)C(O)R^7$, $R^6N(R)S(O)_2R^7$ and $R^6$, $R^6$—O—$R^7$;

$R^5$ is selected from the group consisting of hydroxyl, $(C_1-C_8)$-alkoxy, $(C_5-C_{14})$-aryl-$(C_1-C_8)$-alkoxy-, $(C_1-C_8)$-alkylcarbonyloxy-$(C_1-C_4)$-alkoxy-, $(C_3-C_{14})$-cycloalkoxy and $(C_3-C_{14})$-cycloalkyl-$(C_1-C_8)$-alkoxy-;

$R^6$, $R^{6'}$ independently are selected from the group consisting of $(C_1-C_{14})$-alkyl, $(C_3-C_{14})$-cycloalkyl, $(C_3-C_{14})$-cycloalkyl-$(C_1-C_8)$-alkyl-, $(C_3-C_{14})$-aryl, $(C_5-C_{14})$-aryl-$(C_1-C_8)$-alkyl- and a 3-membered to 7-membered, saturated or unsaturated ring containing one or two heteroatoms, selected from the group consisting of nitrogen, sulfur and oxygen, and is unsubstituted or mono- or disubstituted by a member selected from the group consisting of =O, =S, and $R^8$, where aryl, cycloalkyl and alkyl are optionally substituted once, twice or three times by a member selected from the group consisting of fluorine, chlorine, bromine, -cyano, —$CF_3$, nitro, carboxyl, $(C_1-C_6)$-alkyl, $(C_1-C_6)$-alkoxy, $(C_5-C_{14})$-aryl, $(C_1-C_6)$-alkoxy-$(C_1-C_6)$-alkyl-, $(C_1-C_6)$-alkoxycarbonyl, $(C_1-C_6)$-alkylcarbonyl, $(C_1-C_6)$-alkylaminocarbonyl, $(C_1-C_6)$-alkoxy-$(C_1-C_6)$-alkoxy-, $(C_5-C_{14})$-aryl-$(C_1-C_6)$-alkylcarbonyl, $(C_1-C_6)$-alkanoylamino, $(C_5-C_{14})$-arylsulfonylamino, $(C_1-C_6)$-alkylsulfonylamino, $(C_1-C_6)$-alkylamino, di-$((C_1-C_6)$-alkyl)amino, $(C_1-C_6)$-alkylsulfonyl, $(C_1-C_6)$-alkylaminosulfonyl, $(C_6-C_{14})$-aryl-$(C_1-C_6)$-alkylaminosulfonyl and $(C_5-C_{14})$-aryl-$(C_1-C_6)$-alkylsulfonyl;

$R^7$ are independently $(C_1-C_4)$-alkanediyl or a direct bond;

$R^8$ is selected from the group consisting of $(C1C_{14})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, fluorine, chlorine, bromine, cyano, $CF_3$, nitro, carboxyl, $(C_1-C_6)$-alkoxy, $(C_1-C_6)$-alkoxy-$(C_1-C_6)$-alkyl-, $(C_1-C_6)$-alkoxycarbonyl, $(C_1-C_6)$-alkylcarbonyl, $(C_1-C_6)$-alkylaminocarbonyl, $(C_1-C_6)$-alkoxy-$(C_1-C_6)$-alkoxy-, $(C_5-C_{14})$-aryl-$(C_1-C_6)$-alkylcarbonyl, $(C_1-C_6)$-alkanoylamino, $(C_5-C_{14})$-arylsulfonylamino, $(C_1-C_6)$-alkylsulfonylamino, $(C_1-C_6)$-alkylamino, di-$(C_1-C_6)$-alkylamino, $(C_1-C_6)$-alkylsulfonyl, $(C_1-C_6)$-alkylaminosulfonyl, $(C_6-C_{14})$-aryl-$(C_1-C_6)$-alkylaminosulfonyl and $(C_5-C_{14})$-aryl-$(C_1-C_6)$-alkylsulfonyl; and $R^9$ is hydrogen or $(C_1-C_{14})$-alkyl; comprising reacting a compound of the formula
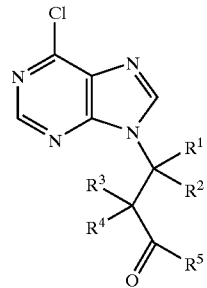
(IV)
with a compound of the formula
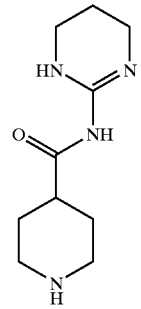
(IX-A)
to give a compound of formula (I-A).
* * * * *